(12) United States Patent
Deppermann

(10) Patent No.: US 9,387,518 B2
(45) Date of Patent: Jul. 12, 2016

(54) SMALL OBJECT SORTING SYSTEM AND METHOD

(75) Inventor: Kevin L. Deppermann, St. Charles, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 1090 days.

(21) Appl. No.: 11/769,318

(22) Filed: Jun. 27, 2007

(65) Prior Publication Data

US 2008/0000815 A1 Jan. 3, 2008

Related U.S. Application Data

(60) Provisional application No. 60/817,062, filed on Jun. 28, 2006.

(51) Int. Cl.
| | |
|---|---|
| B07C 5/00 | (2006.01) |
| B07C 5/38 | (2006.01) |
| B07C 5/342 | (2006.01) |
| B07C 5/36 | (2006.01) |

(52) U.S. Cl.
CPC ............... *B07C 5/38* (2013.01); *B07C 5/3425* (2013.01); *B07C 5/361* (2013.01); *B07C 5/368* (2013.01); *B07C 2501/009* (2013.01)

(58) Field of Classification Search
USPC ............................................. 209/232, 44.1
See application file for complete search history.

(56) References Cited

U.S. PATENT DOCUMENTS

| | | | |
|---|---|---|---|
| 2,756,903 A | 6/1952 | Kreidler | |
| 3,530,372 A | 9/1970 | Laukien | |
| 3,567,075 A * | 3/1971 | Neri | 222/129.4 |
| 3,597,181 A * | 8/1971 | Prendergast | 65/71 |
| 3,642,128 A | 2/1972 | Westwood et al. | |
| 3,743,123 A * | 7/1973 | Kinsbury | 414/564 |
| 3,798,337 A * | 3/1974 | Abalo | 426/279 |
| 3,861,788 A | 1/1975 | Webster | |
| 4,037,970 A | 7/1977 | Webster et al. | |

(Continued)

FOREIGN PATENT DOCUMENTS

| | | |
|---|---|---|
| CL | 673-03 | 2/2004 |
| CL | 2189-05 | 5/2007 |

(Continued)

OTHER PUBLICATIONS

"See Meister Luminar 3076," Brimeose Corporation of America, Baltimore, MD, http://www.brimrose.com/seed_meister.html.

(Continued)

*Primary Examiner* — Stefanos Karmis
*Assistant Examiner* — Michael E Butler
(74) *Attorney, Agent, or Firm* — James E. Davis; Joseph A. Schaper; Harness, Dickey & Pierce, P.L.C.

(57) ABSTRACT

An automated object sorting system is provided. In various embodiments, the automated object sorting system includes an automated object extraction assembly and an automated object collection assembly. The automated object extraction assembly extracts one or more objects from an object sorting tray based on one or more attributes and/or traits of interest. The automated collection assembly selectively deposits the extracted objects in selected collection receptacles according to the particular attributes and/or traits of each respective object.

17 Claims, 14 Drawing Sheets

(56) References Cited

U.S. PATENT DOCUMENTS

| | | | |
|---|---|---|---|
| 4,040,747 A | 8/1977 | Webster | |
| 4,260,262 A | 4/1981 | Webster | |
| 4,278,183 A | 7/1981 | Billington | |
| 4,375,854 A | 3/1983 | Hedel | |
| 4,480,765 A | 11/1984 | Tonus | |
| 4,573,606 A * | 3/1986 | Lewis et al. | 221/2 |
| 4,654,592 A | 3/1987 | Zens | |
| 4,734,584 A | 3/1988 | Rosenthal | |
| 4,752,689 A | 6/1988 | Satake | |
| 4,874,281 A | 10/1989 | Bergerioux | |
| 4,931,061 A | 6/1990 | Young | |
| 5,036,569 A * | 8/1991 | Linnecke | 29/33 K |
| 5,051,699 A | 9/1991 | Hanawa et al. | |
| 5,067,631 A | 11/1991 | Baba | |
| 5,132,538 A | 7/1992 | Norris | |
| 5,193,685 A | 3/1993 | Trevithick | |
| 5,221,518 A | 6/1993 | Mills | |
| 5,253,302 A | 10/1993 | Massen | |
| 5,308,981 A | 5/1994 | Perten | |
| 5,321,212 A | 6/1994 | Wadell | |
| 5,475,221 A | 12/1995 | Wang | |
| 5,533,145 A | 7/1996 | Shofner et al. | |
| 5,584,395 A * | 12/1996 | Homma | 209/571 |
| 5,668,374 A | 9/1997 | DiFoggio et al. | |
| 5,751,421 A | 5/1998 | Wright et al. | |
| 5,764,819 A | 6/1998 | Orr et al. | |
| 5,833,947 A | 11/1998 | Rocklage et al. | |
| 5,837,458 A | 11/1998 | Minshull et al. | |
| 5,864,984 A | 2/1999 | McNertney | |
| 5,904,501 A * | 5/1999 | Ohara et al. | 438/118 |
| 5,918,977 A | 7/1999 | Borggaard et al. | |
| 5,971,162 A | 10/1999 | Allagnat et al. | |
| 5,991,025 A | 11/1999 | Wright et al. | |
| 6,032,571 A * | 3/2000 | Brous et al. | 99/277.2 |
| 6,098,838 A | 8/2000 | Saho et al. | |
| 6,100,526 A | 8/2000 | Mayes | |
| 6,150,158 A | 11/2000 | Bhide et al. | |
| 6,237,286 B1 | 5/2001 | Williames | |
| 6,266,864 B1 | 7/2001 | Barber | |
| 6,377,648 B1 * | 4/2002 | Culbert | 377/6 |
| 6,397,678 B1 | 6/2002 | Popper | |
| 6,537,826 B1 | 3/2003 | Horigane | 436/176 |
| 6,640,428 B2 | 11/2003 | Barber | |
| 6,646,264 B1 | 11/2003 | Modiano et al. | 250/339.07 |
| 6,688,037 B2 | 2/2004 | Keller et al. | |
| 6,705,827 B2 | 3/2004 | Keller et al. | |
| 6,706,989 B2 * | 3/2004 | Hunter et al. | 209/577 |
| 6,809,819 B1 | 10/2004 | Vinjamoori et al. | |
| 7,044,306 B2 | 5/2006 | Deppermann | |
| 7,258,237 B2 | 8/2007 | Nielsen | |
| 7,367,155 B2 | 5/2008 | Kotyk et al. | |
| 7,915,006 B2 * | 3/2011 | Cope et al. | 435/40 |
| 2001/0014750 A1 | 8/2001 | Ulrich et al. | |
| 2002/0144458 A1 | 10/2002 | Hunter et al. | |
| 2004/0072143 A1 | 4/2004 | Timmis et al. | |
| 2004/0221335 A1 | 11/2004 | Shewmaker et al. | |
| 2005/0082207 A1 | 4/2005 | Deppermann | |
| 2005/0137744 A1 | 6/2005 | Winkelmolen et al. | |
| 2006/0042528 A1 | 3/2006 | Deppermann | |
| 2006/0201856 A1 | 9/2006 | Deppermann | |
| 2008/0014073 A1 * | 1/2008 | Moore et al. | 414/796 |

FOREIGN PATENT DOCUMENTS

| | | |
|---|---|---|
| CN | 2724862 Y | 9/2005 |
| EP | 0636310 A1 | 2/1995 |
| EP | 0730164 | 9/1996 |
| EP | 0750188 | 12/1996 |
| EP | 0511184 B1 | 6/1998 |
| EP | 0539537 B2 | 12/2000 |
| EP | 1566434 A2 | 8/2005 |
| GB | 1174480 | 12/1969 |
| GB | 1355612 | 6/1974 |
| WO | WO 94/20230 | 9/1994 |
| WO | WO 9624830 | 8/1996 |
| WO | WO 9700887 | 1/1997 |
| WO | WO 9844140 | 10/1998 |
| WO | WO 9940419 | 8/1999 |
| WO | WO 9941383 | 8/1999 |
| WO | WO 9958959 | 11/1999 |
| WO | WO 0052990 | 9/2000 |
| WO | WO 0071993 A1 | 11/2000 |
| WO | WO 01/22043 A2 | 3/2001 |
| WO | WO 0122043 A2 | 3/2001 |
| WO | WO 0144828 A1 | 6/2001 |
| WO | WO 0189288 A1 | 11/2001 |
| WO | WO 0259586 | 1/2002 |
| WO | WO 0216090 A3 | 2/2002 |

OTHER PUBLICATIONS

Archibald et al., "Development of Short-Wavelength Near-Infrared Spectral Imaging for Grain Color Classification," SPIE vol. 3543, 1998, pp. 189-198.

Bauman, et al., Inheritance of Variation of Oil Content of Individual Corn Kernels, Crop Science, vol. 5, pp. 137-138, 1995.

Daun et al., "Comparison of Three Whole Seed Near-Infrared Analyzers for Measuring Quality Components of Canola Seed," vol. 71, No. 10, 1994, pp. 1063-1068.

Delwiche, "Single Wheat Kernel Analysis by Near-Infrared Transmittance: Protein Content," Analytical Techniques and Instrumentation, vol. 72, No. 1, 1995, pp. 11-16.

Dowell et al., "Automated Single Wheat Kernel Quality Measurement Using Near-Infrared Reflectance," ASAE Annual International Meeting, 1997, paper No. 973022.

Dowell, "Automated Color Classification of Single Wheat Kernels Using Visible and Near-Infrared Reflectance," Cereal Chemistry, vol. 75(1), 1998, pp. 142-144.

Dowell, Floyd E., "An Intelligent Automated System for Determining Peanut Quality," IEEE International Workshop on Intelligent Robot Systems, Jul. 1990.

Dr. Jolanta Soos, "Industrial Process Monitoring Requires Rugged AOTF Tools," Laser Focus World, Aug. 1994.

Gambhir, et al., Simultaneous Determination of Moisture and Oil Content in Oilseeds by Pulsed Muclear Magnetic Resonance, JOACS, vol. 62, No. 1, Jan. 1985.

Guy Rubel, "Simultaneous Determination of Oil and Water Contents in Different Oil Seeds by Pulsed Nuclear Resonance," XP 001080188, JAOCS, vol. 71, No. 10, Oct. 1994.

J.M. Halloin et al., "Proton Magnetic Resonance Imaging of Llpd in Pecan Embryos", XP 001080187, Journal of the American Oil Chemists' Society, vol. 70, No. 12, Dec. 1993.

J.R. Heil, et al., "Magnetic Resonance Imaging and Modeling of WaterUp-take into Dry Beans", XP 002202044, Dept. of Food Science and Technology, University of California, Davis, CA, Jan. 23, 1992.

K. Saito, et al., "Application of Magnetic Resonance Imaging to Non-Destructive Boid Detection in Watermelon," XP000656797, Cryogenics, vol. 36, No. 12, 1996.

M.R. Lakshiminarayana et al., "Spatial distribution of oil in groundnut and sunflower seeds by nuclear magnetic resonance imaging," XP 002201726, J. Biosci., vol. 17, No. 1, Mar. 1992, pp. 87-93.

MacNamara, et al, "Multiplex Sample NMR: an Approach to High-Throughput NMR Using a Parallel Coil Probe," Analytica Chimica Acta; vol. 397, No. 1/03; Elsevier Science B.V.; Oct. 1999, pp. 9-16.

Massie and Norris, "Spectral Reflectance and Transmittance Properties of Grain in the Visible and Near infrared", Transactions of the ASAE, Winter Meeting of the American Society of Agricultural Engineers, 1965, pp. 598-600.

McEntyre, et al., Comparison of Water Absorption Patterns in Two Barley Cultivars, Using Magnetic Resonance Imaging, AACCI, Cereal Chemistry, vol. 76, No. 6, pp. 792-795, 1998.

McGinty, et al., "A System for Automatic Weight Determination of Individual Grain Kernels: Principles and Evaluation", Cereal Science Today, vol. 19, No. 5, May 1974.

Orman and Schumann, "Comparison of Near-Infrared Spectroscopy Calibration Methods for the Prediction of Protein, Oil, and Starch in Maize Grain," J. Agric. Food Chem. vol. 39, 1991, pp. 883-886.

(56) References Cited

OTHER PUBLICATIONS

P.A. Hailey—Pfizer Central Research, "The Role of NIR Spectroscopy in the Measurement of Pharmaceutical Manufacture," http://www.brimrose.com/hailey.html; date unknown.

Paige, et al., "Apparatus for Automatic Measurement of Kernel Weight, Length, and Thickness," Crop Science, vol. 31, pp. 1314-1318, 1991.

Robutti, "Maize Kernel Hardness Estimation in Breeding by Near-Infrared Transmission Analysis," Analytical Techniques and Instrumentation vol. 72, No. 6, 1995, pp. 632-636.

Sander et al., "System for Automatic Weight Determination of Individual Gran Kernels", Transactions of the American Society Agricultural Engineers, vol. 16, No. 6, pp. 1146-1147, Nov./Dec. 1973.

Siebenmorgen, et al., A Data Acquisition/Control System for Individual Kernel and Thin-Layer Grain Drying Research, The American Society of Agricultural Engineers, No. 91-3042, Jun. 1991.

Song et al., Non-invasive Measurement of Moisture Distribution in Individual Wheat Kernels by Magnetic Resonance Imaging, SPIE vol. 2345, Nov. 2-4, 1994.

Yoshida et al., "An Automatic Sequential Single-Seed Weighing System: Variation in Soybean Seed Weight," Journal of the Faculty of Agriculture, Hokkaido University, vol. 61 Pt. 2, 1983.

\* cited by examiner

SMALL OBJECT SORTING SYSTEM AND METHOD

CROSS-REFERENCE TO RELATED APPLICATIONS

This application claims the benefit of U.S. Provisional Application No. 60/817,062, filed on Jun. 28, 2006, the disclosure of which is incorporated herein by reference in its entirety.

FIELD

The present disclosure relates generally to a system and method for sorting small objects, such as seeds, pharmaceutical tablets or capsules, and any other agricultural, manufactured or produced small objects.

BACKGROUND

The sorting of small agricultural, manufactured and/or produced objects such as seeds, pharmaceutical tablets or capsules, small electrical components, ball bearing, small food products, etc., can be cumbersome, painstakingly tedious, and wrought with human error.

For example, in seed breeding, large numbers of seeds are sampled and analyzed to determine whether the seeds possess a particular genotype or traits of interest. Various known systems, devices, tools, and machinery are commonly used to sample a large number of seeds by removing a small portion of each seed, while leaving the remaining seed viable for planting. The removed portions, or chips, and the corresponding 'donor' seeds are then cataloged to track the seeds and the respective corresponding samples. Each sample is then analyzed to identify various attributes of the respective sample and donor seed, such as DNA characteristics and/or traits.

After the seeds are sampled and the samples have been analyzed, the seeds are individually sorted according to attributes of each respective seed. Typically, the sorting process is painstakingly performed by hand, which is extremely time consuming and subject to human error.

BRIEF SUMMARY

An automated object sorting system is provided. In various embodiments, the automated object sorting system includes an automated object extraction assembly and an automated object collection assembly. The automated object extraction assembly extracts one or more objects from an object sorting tray. The automated object extraction assembly then places the extracted objects in a reception end of an object transfer funnel in a selected sequence that is determined based on particular genotype or attributes of each extracted object, e.g., characteristics and/or traits such as size, shape, color, quality, weight composition or genetic traits. The objects traverse the transfer funnel to a disposition end of the transfer funnel. The automated collection assembly selectively positions one or more collection receptacles adjacent the disposition end of the transfer funnel such that the objects are deposited in selected collection receptacles. More particularly, the automated collection assembly positions selected collection receptacles adjacent the disposition end of the transfer funnel in accordance with the sequence that the objects are placed in the reception end of the object transfer funnel. Therefore, the automated object sorting system automatically removes one or more objects from the object sorting tray and selectively deposits the one or more extracted objects in one or more collection receptacles according to the particular attributes of each respective object.

Further areas of applicability of the present disclosure will become apparent from the detailed description provided hereinafter. It should be understood that the detailed description and specific examples, while indicating various embodiments, are intended for purposes of illustration only and are not intended to limit the scope of the present teachings. Furthermore, the features, functions, and advantages of the present disclosure can be achieved independently in various embodiments or may be combined in yet other embodiments.

BRIEF DESCRIPTION OF THE DRAWINGS

The drawings described herein are for illustration purposes only and are not intended to limit the scope of the present teachings in any way.

Corresponding reference numerals indicate corresponding parts throughout the several views of drawings.

DETAILED DESCRIPTION

Figure 1:
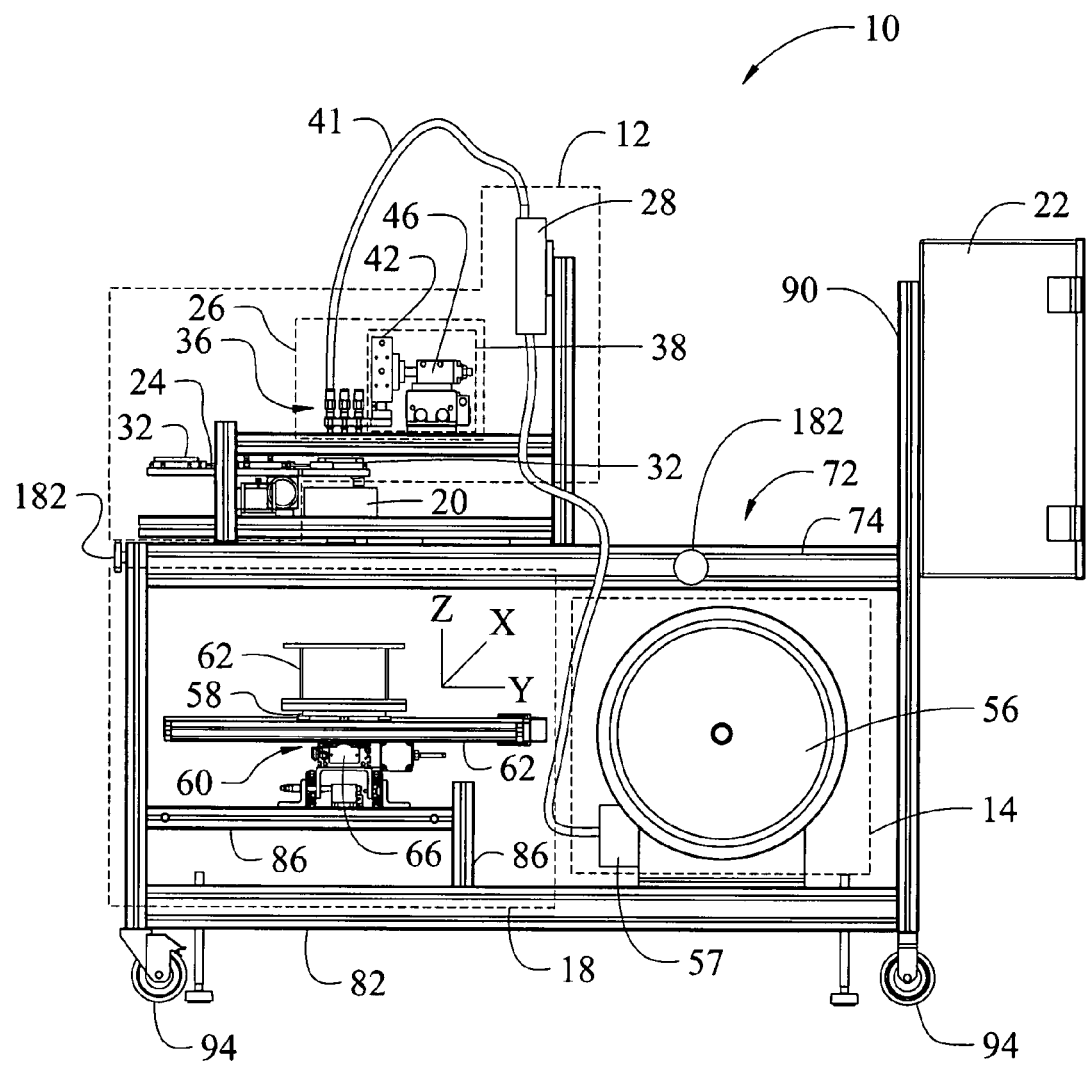
FIG. 1 is a side view of an automated small object sorting system (ASOSS), in accordance with various embodiments.

The following description is merely exemplary in nature and is in no way intended to limit the present teachings, application, or uses. Throughout this specification, like reference numerals will be used to refer to like elements.

Referring to FIG. 1, an automated small object sorting system (ASOSS) 10 is provided for automatically, i.e., robotically, sorting small objects and depositing the sorted objects into selected repositories based on particular genotypes or attributes of each sorted object, e.g., characteristics and/or traits such as size, shape, color, composition, quality, weight, genetic traits, etc. The objects can be any small objects, items, parts or products that are desired to be sorted or separated based on particular attributes of each sorted object. For example, the ASOSS 10 can be utilized to sort such small objects such as seeds and other agricultural products, pharmaceutical tablets or capsules, small electrical components, ball bearing, small food products, etc.

Generally, the ASOSS 10 includes an automated, or robotic, object extraction assembly 12, an air preparation unit 14, an automated, or robotic, object collection assembly 18, a transfer funnel 20 and a computer based master control system (MCS) 22. The transfer funnel is operational to transfer sorted objects from the extraction assembly 12 to the collection assembly 18 and the computer based MCS 22 operates to control the automation, i.e., robotic operation, of the ASOSS 10.

Figure 2:
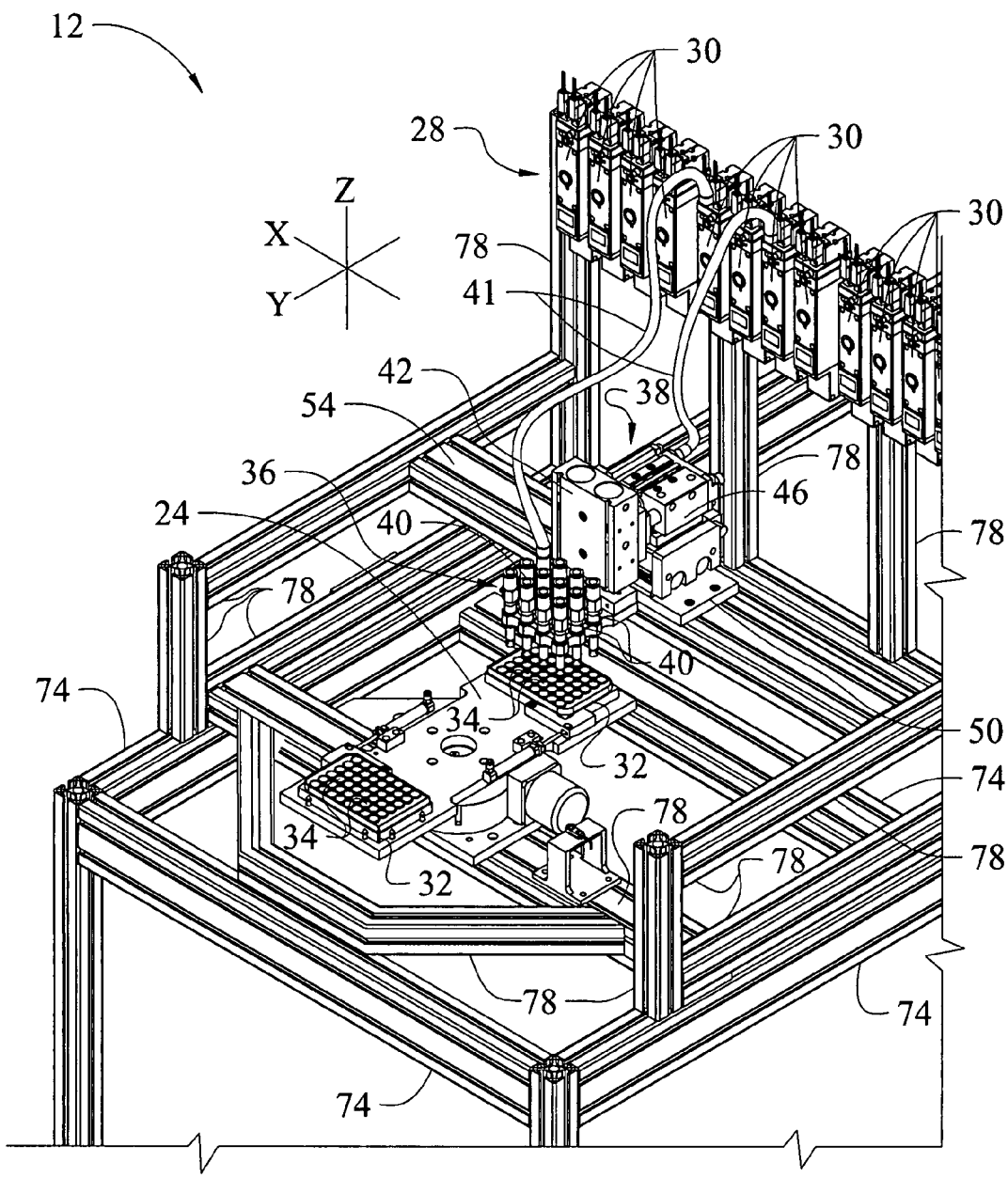
FIG. 2 is an isometric view of an automated object extraction assembly of the ASOSS shown in FIG. 1, in accordance with various embodiments.

Referring also to FIG. 2, in various embodiments, the automated object extraction assembly 12 includes an automated, moveable indexing table 24, an offloading subassembly 26 (shown in FIG. 1) and a bank 28 of regulators 30. Generally, the indexing table is used to support and retain one or more object sorting trays 32 that include a plurality of wells 34, wherein each well 34 is structured retain a single one of the small objects to be sorted. For simplicity and clarity the one or more object sorting trays 32 will be referred to herein as simply the object sorting tray 32. The offloading subassembly 26 operates under the control of the MCS 22 to extract one or more of the objects in the sorting tray wells 34. More particularly, the MCS 22 controls the operation of the regulators 30 that provide, monitor, condition and/or modulate command signals and vacuum pressures to the offloading subassembly 26.

In various embodiments, the offloading subassembly 26 includes at least one nozzle array 36 detachably and interchangeably mounted to a head unit 38. The nozzle array 36 includes a plurality of object extraction nozzles 40 (best illustrated in FIG. 6) geometrically arranged within the nozzle array 36 such that the spacing between adjacent nozzles 40 corresponds with the spacing between adjacent wells 34 of the sorting tray(s) 32. The nozzle array 36 is removably connected to the head unit 38 utilizing any suitable fastening device that will allow the nozzle array 36 to be easily attached to and detached from the head unit 38. For example, the nozzle array 36 can be removably connected to the head unit 38 utilizing locking pins, biased clamps or latches, thumb screws, wing nuts and bolts or any other suitable fastener. Therefore, a first nozzle array 36 having a certain number of nozzles 40, e.g., twelve, of a specific size and spacing, can be easily removed and replaced, i.e., interchanged, with a second nozzle array 36 having a different number of nozzles 40, e.g., twenty-four, of a different specific size and spacing. The head unit 38 is communicatively connected to at least one regulator 30 in the bank 28 of regulators 30.

The one or more regulators 30 communicatively connected to the head unit 38 will simply be referred to herein as the head unit regulator 30. The head unit regulator 30 provides command signals to the head unit 38, via at least one signal transmission line 41, to three-dimensionally move the nozzle array 36 within an X-Y-Z coordinate system above the indexing table 24. As most clearly illustrated in FIG. 2, the head unit 38 includes a Z-axis transition device 42 controlled by the head unit regulator 30 and MCS 22 to transition the nozzle array 36 up and down along the Z-axis. The head unit 38 additionally includes a Y-axis transition device 46 controlled by the head unit regulator 30 and MCS 22 to transition the nozzle array 36 back and forth along the Y-axis. The Z and Y-axis transition devices 42 and 46 can be any devices suitable to independently or simultaneously move the nozzle array 36 along the respective Z and Y axes of the X-Y-Z coordinated system above the indexing table 24. For example, the Z and Y-axis transition devices 42 and 46 can be pneumatically, hydraulically or electrically operated pistons or solenoids.

The head unit 38 further includes a base 50 moveably mounted to an X-axis stage 54 such that the head unit 38 can be moved side-to-side along the X-axis. In various embodiments, the head unit 38 is automatically, or robotically, controlled by the head unit regulator 30 and MCS 22 to transition the nozzle array 36 along the X-axis stage 54 above the indexing table 24. For example, the head unit base 50 can robotically move, as controlled by the MCS 22, along tracks of the X-axis stage 54 utilizing a pneumatically, hydraulically or electrically controlled threaded shaft system, wire or cable pulley system, piston system, or any other suitable positioning system within the X-axis stage 54. In various other embodiments, the head unit 38 is manually moveable along the X-axis stage 54. For example, the head unit base 50 can slide along tracks of the X-axis stage 54 and be held in position using hand adjustable locking devices such as clamps, wing nuts and bolts, or pins.

In various embodiments, the head unit regulator 30 is a pneumatic regulating device that provides pneumatic command signals to the head unit 38 over one or more pneumatic signal transmission lines 41, i.e., pneumatic flex tubes. The head unit pneumatic regulator 30 regulates the pneumatic command signals e.g., vacuum and/or expansion pressure signals, sent to the head unit 38 via the pneumatic flex tube. Particularly, as controlled by the MCS 22, the head unit pneumatic regulator 30 provides, monitors, conditions and/or modulates the pneumatic command signals sent to the head unit 38. The pneumatic command signals control the operation of the Z and Y-axis transition devices 42 and 46, and in some embodiments, the X-axis stage 54, to two-dimensionally or three-dimensionally move the nozzle array 36 within the X-Y-Z coordinate system. In such pneumatic embodiments, the ASOSS 10 is connected to a vacuum source (not shown). The vacuum source can be included in the ASSOS 10 or remotely located from the ASOSS 10. That is, the vacuum source can be located within the structure of the ASOSS 10 or the ASSOS 10 can be connected to a vacuum source located remotely from the ASOSS 10. In various pneumatic embodiments, the pneumatic signals are generated by the air preparation unit 14.

Referring now to FIG. 1, the air preparation unit 14 generally includes a ballast tank 56 and an air filter 57. The ballast tank 56 stores air provided by the vacuum source to aid in the regulation of the various pneumatic signals used to operate the ASOSS 10, as described herein, and assist in providing a constant, steady air supply to the various components and assemblies of the ASOSS 10. The air filter 57 filters the air provided by the ballast tank 56 to the various components and assemblies of the ASOSS 10. For example, air provided by the air preparation unit 14, to generate vacuum pressures communicated to the regulators 30 that operate the nozzles 40, as described below, is regulated, conditioned and filtered by the ballast tank 56 and the air filter 57.

Referring again to FIG. 2, in various other embodiments, the head unit regulator 30 can command movement of the nozzle array 36 using any other suitable command signal and corresponding signal transmission line(s) 41. For example, the head unit regulator 30 can command movement of the nozzle array 36 using electronic signals, wireless (e.g., electromagnetic) signals, hydraulic signals, optical signals or any other suitable command signals. For simplicity and clarity not all signal transmission lines 41 are shown in FIG. 2. More particularly, it will be recognized that the various figures described herein do not illustrate each and every component and/or part of the ASOSS 10. Certain components and/or parts, e.g., the head unit signal transmission line(s) 41, are not illustrated in the various figures in order to reveal other, more important, components and/or parts to simplify the illustration and allow for a better understanding of how the ASOSS 10 is constructed and operates.

Figure 3:
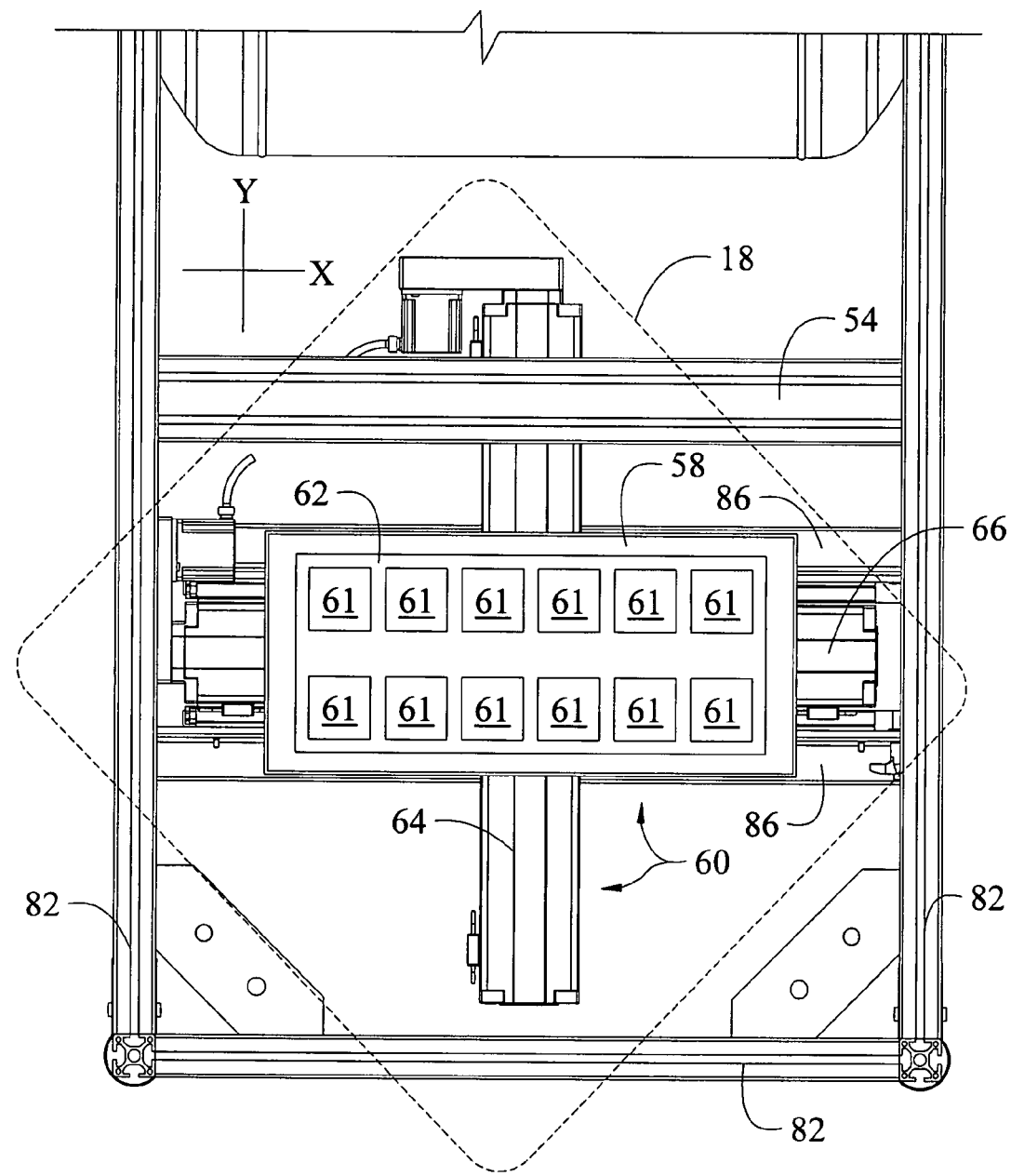
FIG. 3 is a top view of an automated collection assembly of the ASOSS shown in FIG. 1, in accordance with various embodiments.

Referring particularly to FIGS. 1 and 3, in various embodiments, the automated collection assembly 18 includes a collection assembly platform 58 and a collection assembly X-Y stage 60. The collection assembly platform 58 is connected to the collection assembly X-Y stage 60. The X-Y stage is controllable by the MCS 22 to automatically, or robotically, move the collection assembly platform 58 within the X-Y plane of the X-Y-Z coordinate system. The collection assembly platform 58 is structured to removably retain a receptacle retention apparatus 62 configured to include or retain a plurality of receptacles 61 adapted to receive and retain objects transferred from the extraction assembly 12 to the collection assembly 18, via the transfer funnel 20, as described below. The collection assembly X-Y stage 60 includes a Y-axis transport 64 and an X-axis transport 66. The Y-axis transport 64 is automatically, or robotically controllable by the MCS 22 to move the collection assembly platform 58 along the Y-axis of the X-Y-Z coordinate system. Thus, under the control of the MCS 22, the collection assembly platform 58 and associated receptacle retention apparatus 62 can be automatically positioned anywhere along the length of the Y-axis transport 64. Additionally, the Y-axis transport 64 is movably connected to the X-axis transport 66 of the collection assembly X-Y stage 60. Under the control of the MCS 22, the Y-axis transport 64, the collection assembly platform 58 and associated receptacle retention apparatus 62 can be automatically positioned anywhere along the length of the X-axis transport 66. Therefore, receptacle retention apparatus 62 can be automatically, or robotically, moved in the X and/or Y directions to position any desired portion or section of the receptacle retention apparatus 62 substantially adjacent the transfer funnel to receive one or more objects extracted from the sorting tray 32 by the extraction assembly 12, as described further below.

Figure 3A:
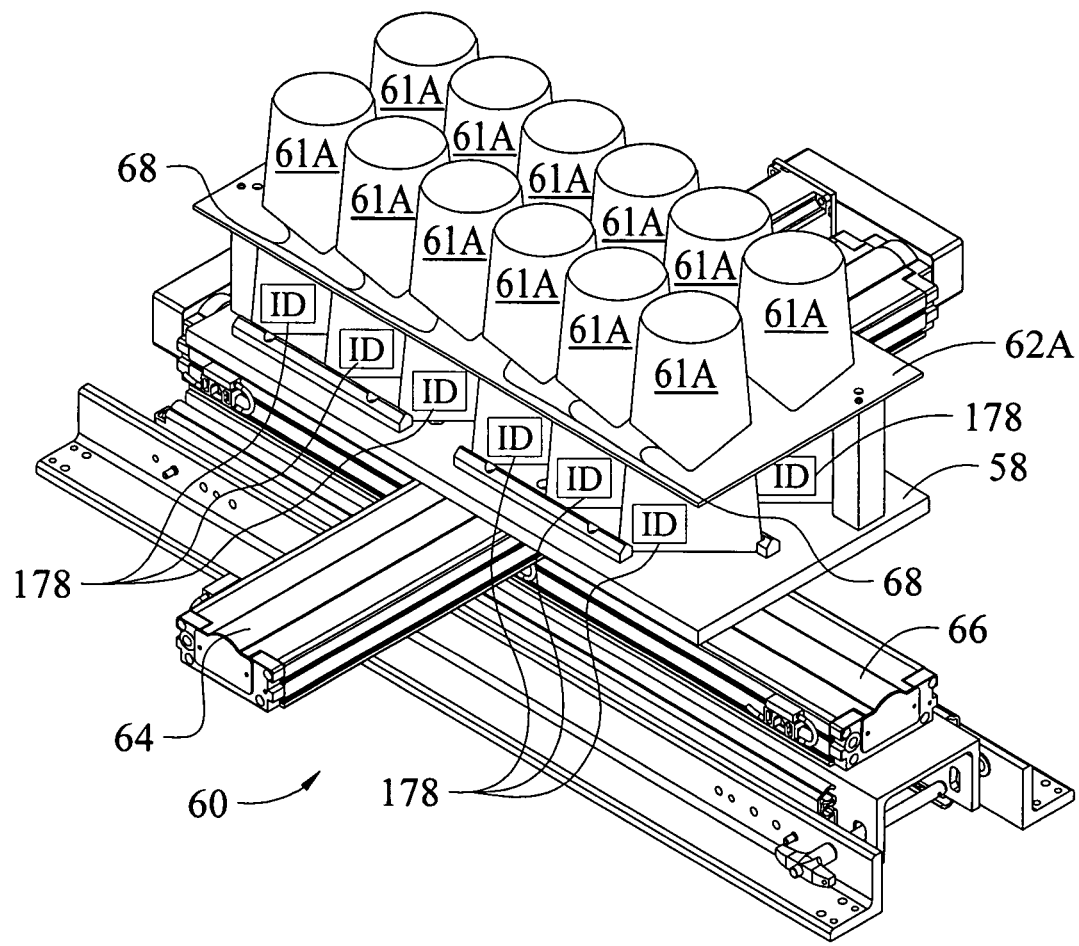
FIG. 3A is an isometric view of a multi-receptacle collection table removably coupled to an X-Y stage of the ASOSS shown in FIG. 1, in accordance with various embodiments.

Referring now to FIG. 3A, in various embodiments the receptacle retention apparatus 62 can be a multi-receptacle collection table 62A removably positioned on, or connected to, the collection assembly platform 58. The multi-receptacle collection table 62A includes a plurality of bins 68 structured to retain a plurality of the collection receptacles 61A. The collection receptacles 61A can be any type of collection devices, apparatus or structures suitable for receiving objects extracted from the sorting tray 32 by the offloading subassembly 26 and deposited into the transfer funnel 20. For example, the collection receptacles 61A can comprise envelopes, containers, tubes, cups, boxes or any other vessel suitable for receiving and retaining objects transferred from the extraction assembly 12 to the collection receptacles 61A, via the transfer funnel 20.

Figure 3B:
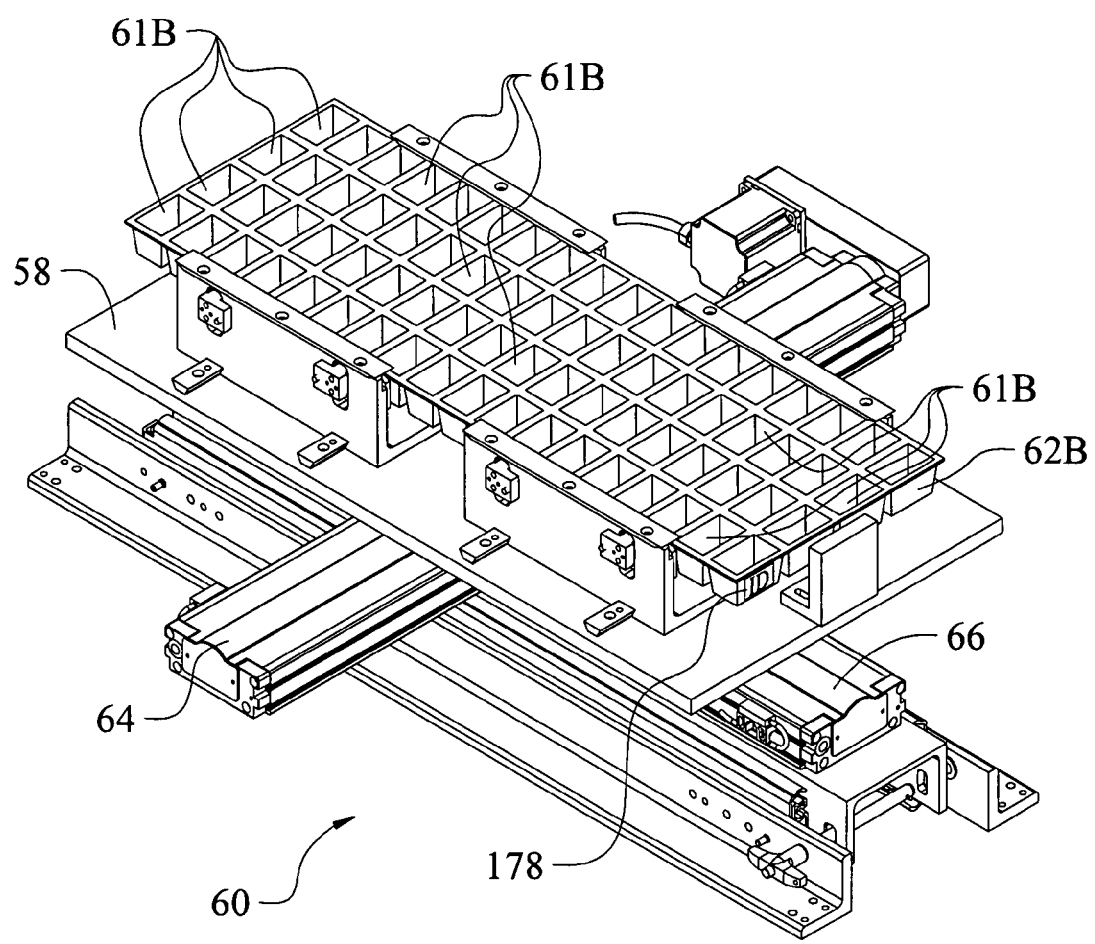
FIG. 3B is an isometric view of an indexing tray removably coupled to an X-Y stage of the ASOSS shown in FIG. 1, in accordance with various other embodiments.

Referring to FIG. 3B, in various other embodiments the receptacle retention apparatus 62 can be a multi-reservoir indexing tray 62B removably positioned on, or connected to, the collection assembly platform 58 and the receptacles 61 can be a plurality of object reservoirs 61B included in the multi-reservoir indexing tray 62B. The plurality of object reservoirs 61B are structured to receive and retain objects extracted from the sorting tray 32 by the offloading subassembly 26 and deposited into the transfer funnel 20.

Figure 3C:
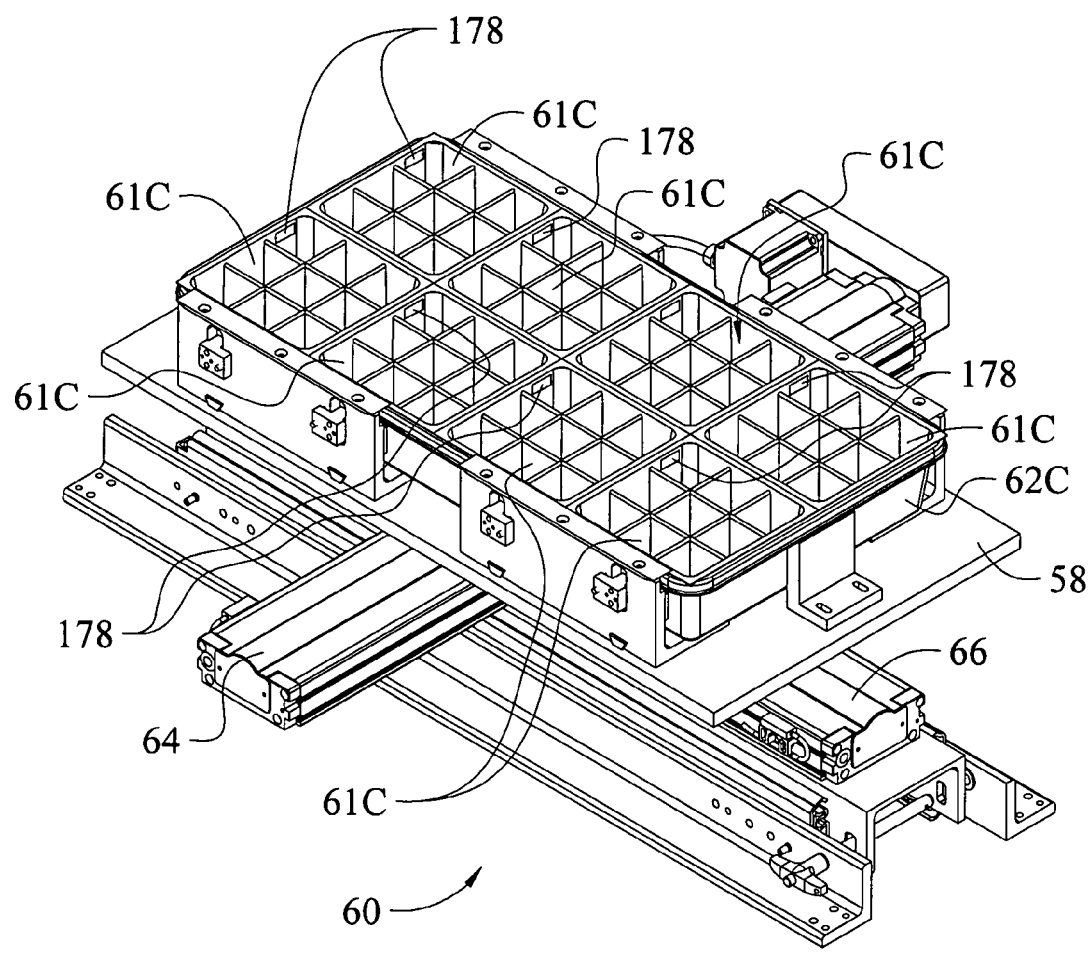
FIG. 3C is an isometric view of a planter tray removably coupled to an X-Y stage of the ASOSS shown in FIG. 1, in accordance with yet other various embodiments.

Referring to FIG. 3C, in various embodiments wherein the objects to be sorted are agricultural products such as seeds, the receptacle retention apparatus 62 can be a multi-container planter tray 62C removably positioned on, or connected to, the collection assembly platform 58. Additionally, the receptacle 61 can comprise one or more planting containers 61C. The multi-container planter tray 62C includes a plurality of the planting containers 61C that can contain soil or other organic compound. Therefore, seeds extracted from the sorting tray 32 by the offloading subassembly 26 and deposited into the transfer funnel 20 can be automatically deposited into the planting containers 61C filled with soil or other organic compound.

Referring now to FIGS. 1, 2 and 3, to properly locate and position the extraction assembly 12, transfer funnel 20 and collection assembly 18 with respect to each other, the extraction assembly 12, the collection assembly 18 and the transfer funnel 20 are connected, or mounted, to an ASOSS framework structure 72 (generally indicated in FIG. 1). In various embodiments, the extraction assembly 12 is generally mounted to an upper main frame 74 and an extraction assembly chassis 78 mounted to the upper main frame 74, as best illustrated in FIG. 2. Similarly, the collection assembly 18 is generally mounted to a lower main frame 82 and a collection assembly chassis 86 mounted to the lower main frame 82, as best illustrated in FIGS. 1 and 3. The MCS 22 can be mounted to the ASOSS framework structure 72, for example, mounted to a head frame structure 90, best shown in FIG. 1, or located separately from ASOSS framework structure 72. In various embodiments, the ASOSS 10 is substantially stationary such that it is relatively fixed in one location. In various other embodiments, as illustrated in FIG. 1, the framework structure 72 of ASOSS 10 can include wheels 94 such that the ASOSS 10 is portable and can be easily moved from one location to another.

In various embodiments, the collection assembly X-Y stage 66, particularly the X and Y-axis transports 66 and 64, are each communicatively connected to at least one regulator 30 in the bank 28 of regulators 30. The regulators 30 communicatively connected to the collection assembly X-Y stage 66 will simply be referred to herein as the collection assembly stage regulators 30. As controlled by the MCS 22, the collection assembly stage regulators 30 provide command signals to the X and Y-axis transports 66 and 64, via signal transmission lines 41 to two-dimensionally move the collection assembly platform 58 and receptacle retention apparatus 62 within the X-Y plane of the X-Y-Z coordinate system below the extraction assembly 12.

The collection assembly platform 58 and receptacle retention apparatus 62 are transitioned along the Y-axis transport 64 using any suitable system, device or apparatus. For example, the collection assembly platform 58 and receptacle retention apparatus 62 can be robotically transitioned, as controlled by the MCS 22, along the Y-axis transport 64 utilizing a pneumatically, hydraulically or electrically controlled threaded shaft system, wire or cable pulley system, piston system or any other suitable positioning system within the Y-axis transport 64. Similarly, the Y-axis transport 64, collection assembly platform 58 and receptacle retention apparatus 62 are transitioned along the X-axis transport 66 using any suitable system, device or apparatus. For example, the Y-axis transport 64, collection assembly platform 58 and receptacle retention apparatus 62 can be robotically transitioned, as controlled by the MCS 22, along the X-axis transport 66 utilizing a pneumatically, hydraulically or electrically controlled threaded shaft system, wire or cable pulley system, piston system or any other suitable positioning system within the X-axis transport 66.

In various embodiments, the collection assembly stage regulators 30 are pneumatic regulating devices that provide pneumatic command signals to the X and Y transports 66 and 64 via the pneumatic signal transmission lines, i.e., pneumatic flex tubes. The collection assembly stage regulators 30 regulate the pneumatic command signals e.g., vacuum and/or expansion pressure signals, sent to the X and Y transports 66 and 64 via the pneumatic flex tube. Particularly, the collection assembly stage regulators 30 provide, monitor, condition and/or modulate the pneumatic command signals sent to the X and Y transports 66 and 64, i.e., the collection assembly X-Y stage 66. The pneumatic command signals control the operation of the X and Y transports 66 and 64 to two-dimensionally move the collection assembly platform 58 within the X-Y plane of the X-Y-Z coordinate system.

In various other embodiments, the collection assembly stage regulators 30 can command movement of the collection assembly X-Y stage 66 using any other suitable command signal and corresponding signal transmission line(s). For example, the collection assembly stage regulators 30 can command movement of the collection assembly X-Y stage 66 using electronic signals, wireless (e.g., electromagnetic) signals, hydraulic signals, optical signals or any other suitable command signals. For simplicity and clarity the signal transmission line(s) are not shown.

Figure 4:
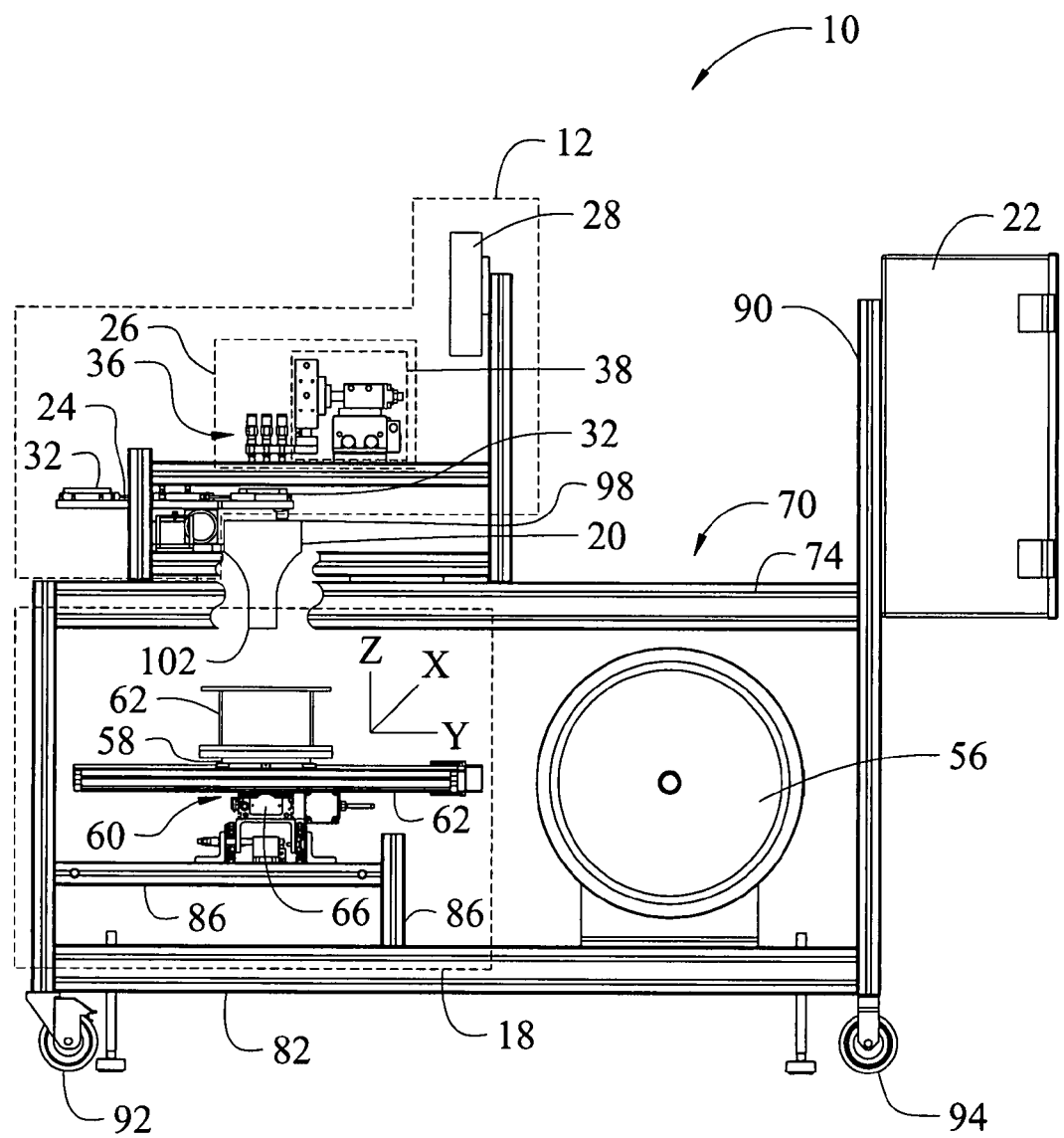
FIG. 4 is a side view of the ASOSS shown in FIG. 1 with a portion of an upper main frame and extraction assembly chassis cut away to illustrate a transfer funnel of the ASOS, in accordance with various embodiments.
Figure 5:
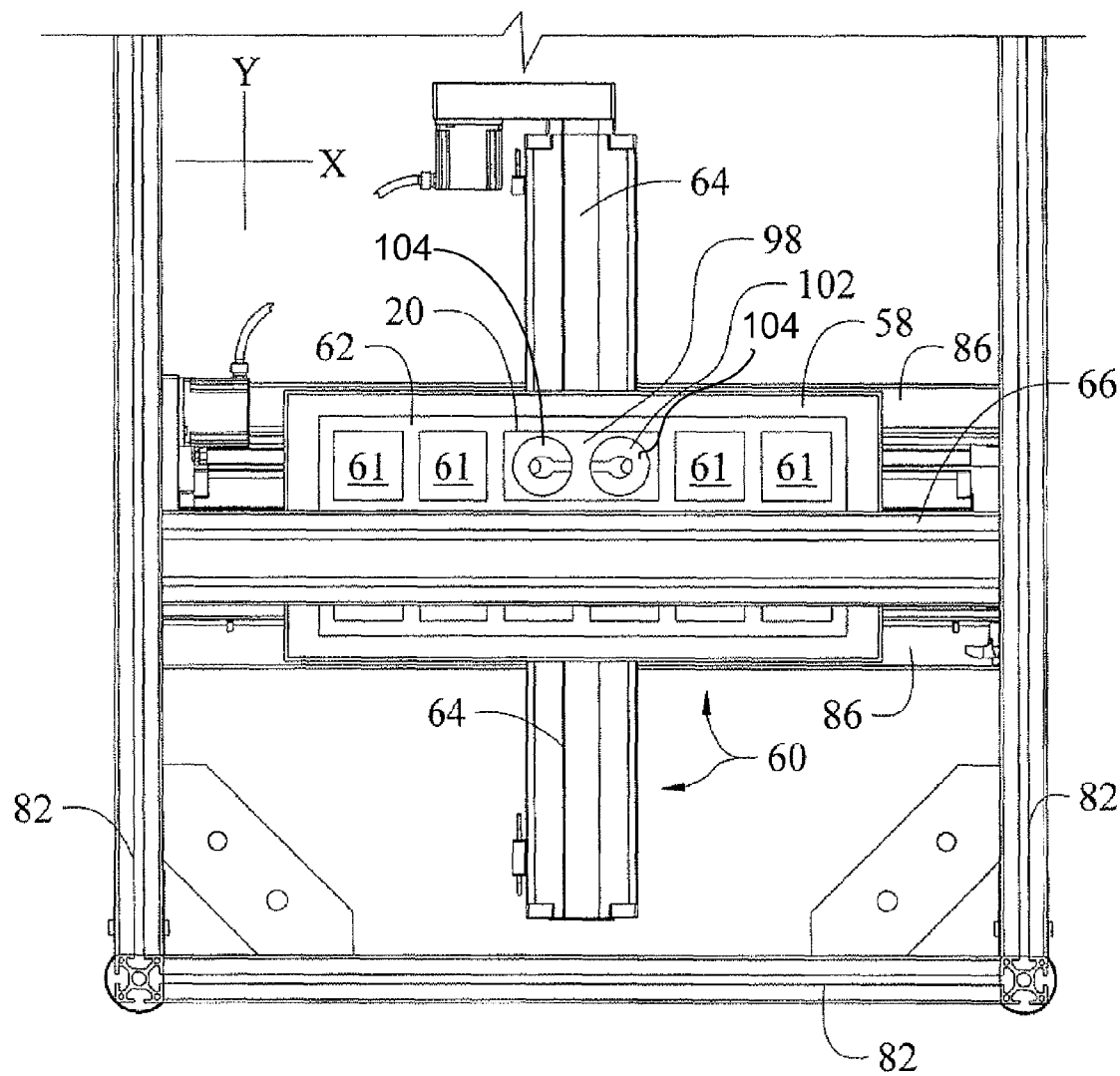
FIG. 5 is a top view of the ASOSS shown in FIG. 1 illustrating a disposition end of the transfer funnel, in accordance with various embodiments.

Referring now to FIGS. 4 and 5, the transfer funnel 20 includes a reception end 98 substantially adjacent the nozzle array 36 structured to receive the one or more objects extracted from the object tray 32 by the offloading subassembly 26. Once the objects are placed in the reception end 98, the objects are funneled through the transfer funnel to a disposition end 102 of the transfer funnel 20. The disposition end 102 is substantially adjacent the receptacle retention apparatus 62. More particularly, the disposition end 102 of the transfer funnel 20 is substantially adjacent a specific one of the collection receptacles 61 retained within the bins 68 that has been robotically positioned substantially adjacent the disposition end 102, via the collection assembly X-Y stage, as commanded by the MCS 22. The transfer funnel 20 can transfer the one or more objects from the reception end 98 to the disposition end 102 using any suitable means of conveyance. For example, in various embodiments, as shown in FIG. 4, the transfer funnel can utilize gravitational forces to transfer the one or more objects from the reception end 98 to the disposition end 102. In such embodiments, the nozzle array 36 would drop the selected one or more objects extracted from the object tray 32 by the nozzle array 36 into the reception end 98 of the transfer funnel 20. Gravitational forces cause the one or more objects to travel through the transfer funnel 20 and be directed by the transfer funnel 20 into a specific one of the receptacles 61 retained within the bins 68 that has been robotically positioned substantially adjacent the disposition end 102, via the collection assembly X-Y stage, as commanded by the MCS 22.

Although FIGS. 4 and 5 illustrate the transfer funnel 20 structured to utilize gravitational forces to transfer the one or more objects from the reception end 98 to the disposition end 102, other means of conveyance are envisioned and within the scope of the present disclosure. In various embodiments, the ASOSS 10 can implement mechanically generated forces to convey or transfer the one or more objects from the reception end 98 to the disposition end 102. For example, the ASOSS 10 can utilize pulsed or forced air to 'blow' the one or more objects from the reception end 98 to the disposition end 102. Alternatively, the ASOSS 10 can utilize suction or vacuum forces to 'draw' the one or more objects from the reception end 98 to the disposition end 102. Or, the ASOSS 10 can utilize any suitable mechanical conveyor system to 'transport' the one or more objects from the reception end 98 to the disposition end 102.

Referring particularly to FIG. 5, the transfer funnel 20 can include one or more internal passages 104 that direct the one or more objects from the reception end 98 to the disposition end 102. For example, as illustrated in FIG. 5, the transfer funnel 20 can include two internal passages 104 that reduce the amount of automated movement needed by the collection assembly X-Y stage 66 to position the automatically selected receptacle substantially adjacent the disposition end 102 of the transfer funnel 20. For example, if the receptacle retention apparatus 62 were considered to be divided into two halves, such as a left side and a right side, the receptacles 61 residing in the bins 68 on the left side of the receptacle retention apparatus 62 would receive objects deposited into the 'left side' transfer funnel internal passage 104. Conversely, the receptacles 61 residing in the bins 68 on the right side of the receptacle retention apparatus 62 would receive objects deposited into the 'right side' transfer funnel internal passage 104. Accordingly, the collection assembly X-Y stage 66 only needs to move distances in the X and Y direction sufficient to position the 'left side' receptacles 61 substantially adjacent the 'left side' internal passage 104, and the 'right side' receptacles 61 substantially adjacent the 'right side' internal passage 104. The terms 'left side' and 'right side' are merely exemplary and are not intended to limit the scope of the present disclosure. Other exemplary terms such as 'front side' and 'back side', 'forward' and 'aft' and 'first side' and 'opposing second side' could also be used and remain within the scope of the present disclosure.

In various other embodiments, the ASOSS 10 is structured such that the transfer funnel 20 is mounted to a positioning device, similar to the nozzle array head unit 38 or the collection assembly X-Y stage 66, to position, or assist in positioning, the particular receptacle, as selected by the MCS 22, substantially adjacent the disposition end 102 of the transfer funnel 20.

Figure 6:
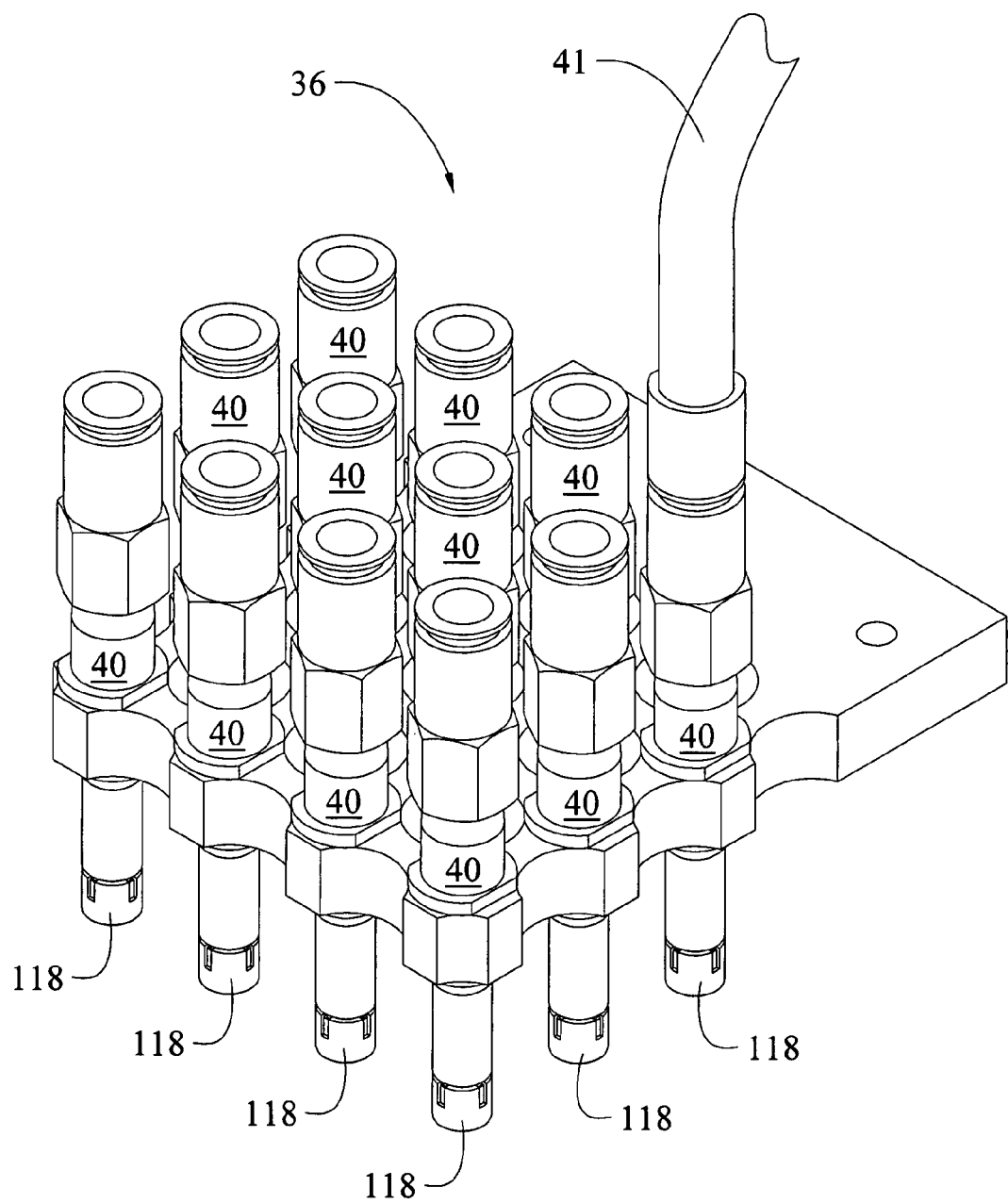
FIG. 6 is an isometric view of a nozzle array of the ASOSS shown in FIG. 1, in accordance with various embodiments.

Referring to FIGS. 2 and 6, each of the nozzles 40 of the nozzle array 36 are communicatively connected to at least one regulator 30 in the regulator bank 28. The regulators 30 communicatively connected to the nozzles 40 will simply be referred to herein as the nozzle regulators 30. As controlled by the MCS 22, the nozzle regulators 30 provide vacuum signals to each of the nozzles 40, via signal transmission lines 41, to activate the nozzles 40, as described below. More particularly, the nozzle regulators 30 are vacuum pressure regulators that monitor, condition and/or modulate vacuum signals communicated to each of the nozzles 40 via the signal transmission lines 41, i.e., vacuum flex lines 41. Generally, the nozzle regulators 30 include switches, valves, and sensors to control and regulate the vacuum pressure for each nozzle 40.

In various embodiments, the air supply and ballast tank 56 are used to generate the vacuum pressures, i.e., vacuum signals, regulated and communicated to the nozzles 40 by the nozzle regulators 30. As set forth above, for simplicity and clarity, not all signal transmission lines 41 are shown in the various figures. Thus, although it should be understood that each nozzle 40 shown in FIGS. 2 and 6 is communicatively connected to at least one nozzle regulator 30 via a vacuum flex line 41, for simplicity and clarity, only a single vacuum flex line 41 is illustrated in FIG. 6.

Figure 7:
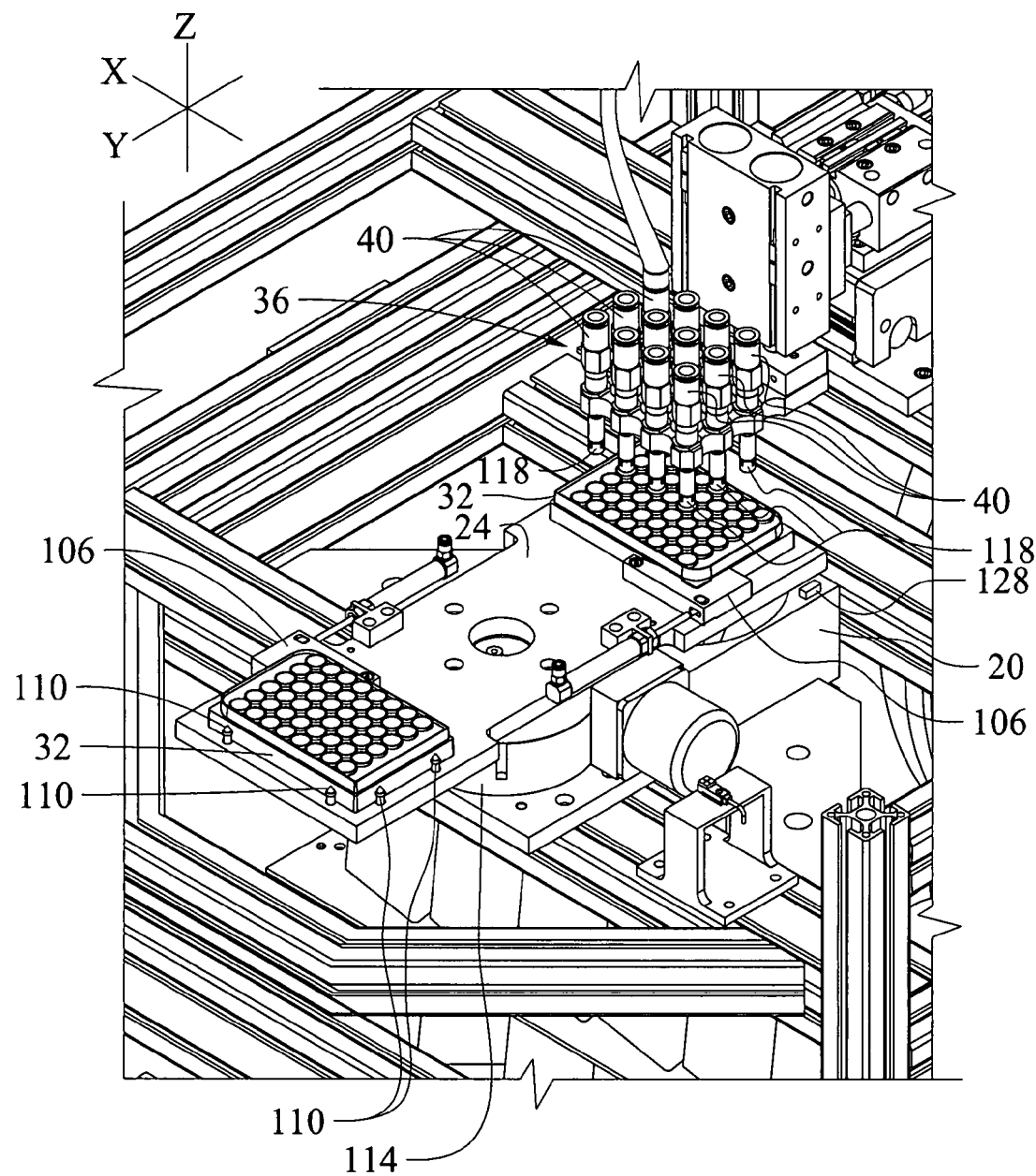
FIG. 7 is an isometric view of a rotary indexing table of the ASOSS shown in FIG. 1, in accordance with various embodiments.

Referring to FIG. 7, in various embodiments, the automated, moveable indexing table 24 includes at least one sorting tray retention device 106 that holds, or retains, the one or more sorting trays 32 in position on the indexing table 24 during operation of the ASOSS 10. The sorting tray retention device(s) 106 can be any retention device suitable to substantially fixedly hold the sorting tray(s) 32 in position on the indexing table 24 while the offloading subassembly 26 extracts selected objects from the sorting tray(s) 32, as described below. Additionally, the retention device(s) 106 can be manually operated or automatically operated by the MCS 22. For example, the retention device(s) 106 can be one or more manually operated thumb screws, clamps, latches, snaps, magnetic clasps, pins or biased levers. Alternatively, the retention device(s) 106 can be one or more pneumatic, hydraulic or electrically driven clamps, latches or levers controlled by the MCS 22. In various embodiments, as illustrated in FIG. 7, each retention device(s) 106 is a robotically operated lever device, controlled by the MCS 22 to exert a force on at least one side of the respective sorting tray 32 sufficient to substantially fixedly retain the sorting tray 32 against a plurality of retention pins 110 connected to the indexing table 24.

In various embodiments, the automated, moveable indexing table 24 is a rotary indexing table 24 adapted to rotate, or pivot, within the X-Y plane of the X-Y-Z coordinate system such that opposing ends of the indexing table 24 can be alternately positioned under the nozzle array 36, as controlled by the MCS 22. Accordingly, the offloading subassembly 26 can be extracting objects from a sorting tray 32 supported at one end of the rotary indexing table 24 while a second loaded sorting tray 32 is substantially simultaneously being positioned on the opposing end of the rotary indexing table 24. Any suitable rotary drive device 114, controllable by the MCS 22, can be utilized to rotate, or pivot, the rotary indexing table 24. For example, the rotary drive device 114 can be a pneumatically, hydraulically, or electrically driven rotary drive device or motor controllable by the MCS 22. The MCS 22 controls rotation of the rotary indexing table 24 to selectively position, i.e., rotate and stop, either end of the rotary indexing table 24 at any point along a 360° circumference of rotation.

In various embodiments, the MCS 22 rotates the rotary indexing table 24 such that a loaded sorting tray 32, i.e., a sorting tray 32 having an object retained within some or all the wells 34, is positioned under the nozzle array 36 and above the transfer funnel 20. Then, as described further below, the MCS 22 commands the head unit 38 to lower the nozzle array 36 such that a tip 118 of each nozzle 40 (best illustrated in FIG. 6) is inserted into a corresponding well 34 of the sorting tray 32. The MCS 22 then commands one or more selected nozzle regulators 30 to communicate a vacuum pressure, i.e., suction, at the tip 118 of at least one of the nozzles 40. More specifically, one, some or all of the nozzles 40 can be activated by the MCS 22, i.e., provided with a vacuum pressure at the respective tip 118. Utilizing the vacuum pressure, the selected nozzles 40 capture, i.e., grasp, and retain one or more selected objects in corresponding wells 34 of the sorting tray 32. More specifically, one, some or all of the objects in the corresponding wells 34 can be captured and retained by the nozzle array 36. The MCS 22 controls the operation of the nozzle regulators 30 such that the vacuum pressure provided at the tip 118 of each nozzle 40 is modulated to exert sufficient force to capture the respective object without damaging the respective object. The MCS 22 then commands the head unit 38 to lift, or raise, the nozzle array 36, thereby extracting the selected objects from the object sorting tray 32. The MCS 22 then rotates the rotary indexing table 24 to move the end of the rotary indexing table 24 and the sorting tray 32 being offloaded sufficiently out of the way, e.g., approximately 90°, to provide an unobstructed path between the nozzle array 36 and the transfer funnel reception end 98.

The MCS 22 then commands selected ones of the activated nozzles 40 to deactivate, i.e., terminate the vacuum pressure supplied to selected activated nozzles 40, thereby releasing the respective object(s) into the reception end 98 of the transfer funnel 20. In various embodiments, before releasing the object(s), the MCS 22 commands the head unit 38 to move the nozzle array 36 toward the transfer funnel 20. Prior to releasing the selected extracted objects, the MCS 22 commands the collection assembly X-Y stage 66 to position a selected one of the receptacles 61 retained in the receptacle retention apparatus 62 adjacent, e.g., under, the disposition end 102 of the transfer funnel 20. Thus, the selected extracted object(s) is/are deposited in a selected receptacle 61. Furthermore, the selected extracted object(s) is/are deposited in the selected receptacle(s) 61 based on the specific attributes of the selected extracted object(s).

More particularly, the MCS 22 deactivates one, some or all of the nozzles 40 to release one, some or all the extracted objects into the reception end 98 of the transfer funnel 20. If not all the extracted objects are to be released and deposited into one selected receptacle, the MCS 22 will command the offloading subassembly 26 to release selected ones of the extracted objects into a selected receptacle, as described above. The MCS 22 will then command the collection assembly X-Y stage 66 to position a second selected receptacle adjacent the disposition end 102 of the transfer funnel 20 and release at least one of the remaining extracted objects. Thus, the at least one extracted object remaining after the first disposition of selected extracted objects will be deposited into the second selected receptacle, based on the specific attributes of the selected extracted object(s). The MCS 22 will continue to reposition the collection assembly X-Y stage 66, and selectively release and deposit the remaining extracted objects in selected receptacles 61 based on the attributes of each extracted object.

Furthermore, as described above, one, some or all of the objects in the sorting tray 32 can be extracted at one time. If not all the objects in the sorting tray 32 are extracted during the first extraction process, but it is desired to selectively extract and deposit other objects remaining in the sorting tray 32, the MCS 22 will command repetition of the offloading process, as described above. That is, once the offloading subassembly 26 selectively releases all the objects extracted during a first extraction process, the MCS 22 will rotate the rotary indexing table 24 to reposition the sorting tray 32 under the nozzle array 36. The MCS 22 with then command a second selective extraction and disposition of other objects in the sorting tray 32 in the same manner as described above. The MCS 22 will continue to command subsequent selective extraction and disposition processes until all the desired objects in the sorting tray 32 have been selectively extracted and deposited into selected receptacles 61 based on the attributes of the respective selected objects.

Furthermore, depending on the number of wells 34 in the sorting tray 32 being offloaded and the corresponding number of nozzles 40 in the nozzle array 36, the MCS 22 can reposition the nozzle array 36 to selectively extract all the desired objects in the respective sorting tray 32 and deposit the extracted objects into selected receptacles 61. More particularly, if the number of wells 34 in the sorting tray 32 is greater than the number of nozzles 40 in the nozzle array 36, the MCS 22 will command the head unit 38 to reposition the nozzle array 36 in the X and/or Y direction during subsequent extraction processes. For example, if the sorting tray 32 includes forty-eight wells 34, but the nozzle array 36 only includes twelve nozzles 40, then initially, when the sorting tray 32 is positioned under the nozzle array 36, only twelve of the wells 34 will align with a respective one of the twelve nozzles 40. Thus, after the offloading subassembly 26 selectively extracts and deposits the selected ones of the twelve 'aligned' objects, the MCS 22 will move the nozzle array 36 along the X and/or Y-axis to align the twelve nozzles 40 with a second set of twelve wells 34. The MCS 22 commands repetition of the offloading and nozzle array realignment process until all desired objects in the forty-eight wells 34 have been deposited in the selected receptacles 61 based on the attributes of the respective selected objects.

Figure 8:
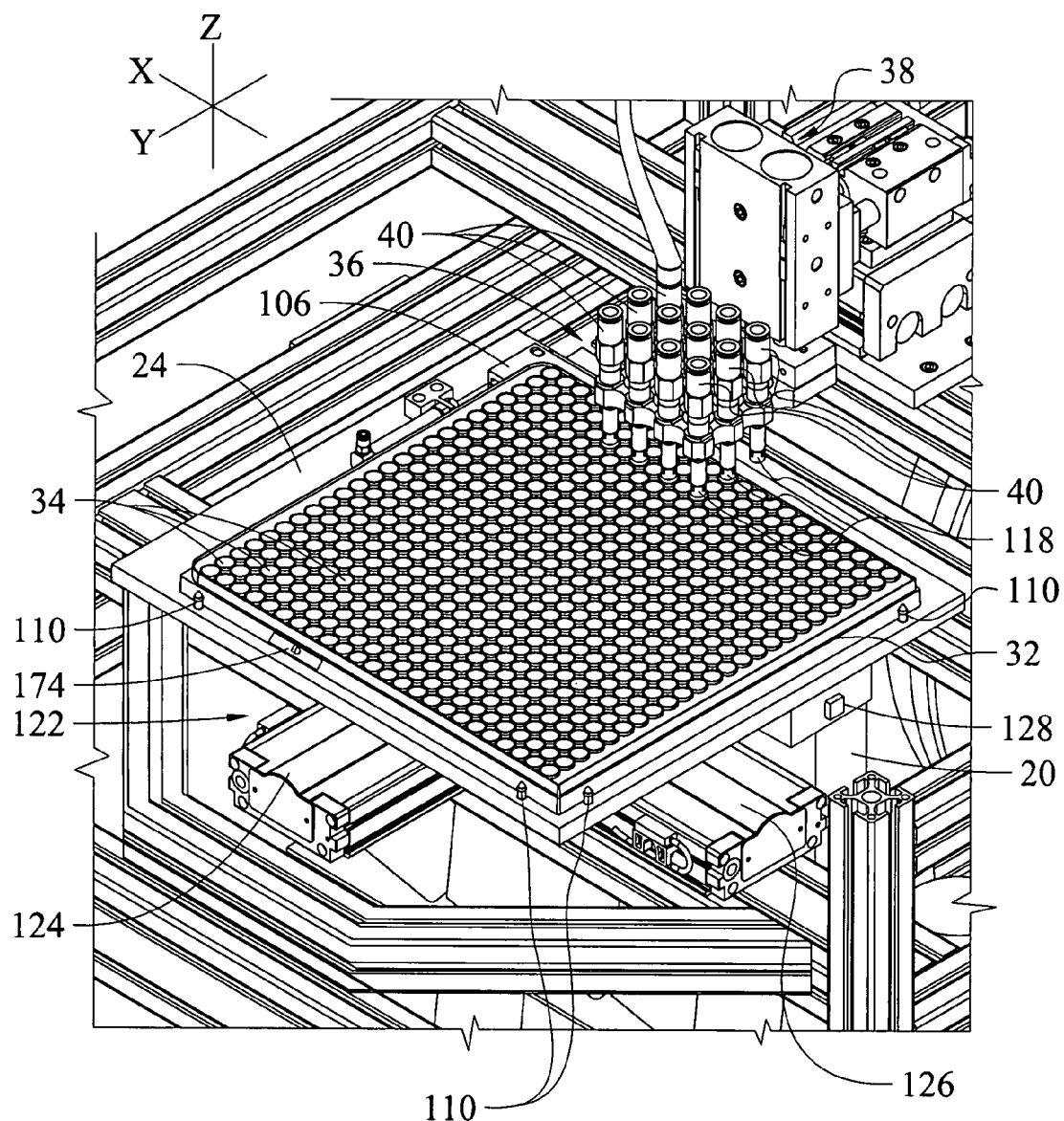
FIG. 8 is an isometric view of a staged indexing table of the ASOSS shown in FIG. 1, in accordance with various embodiments.

Referring to FIG. 8, in various embodiments, the automated, moveable indexing table 24 is a staged indexing table 24 mounted to an indexing table X-Y stage 122 adapted to move the staged indexing table 24 within the X-Y plane of the X-Y-Z coordinate system. The staged indexing table 24 is suitable for supporting and retaining one or more sorting trays 32. The sorting tray(s) 32 can be retained on the staged indexing table 24 using any suitable retention device, as described above.

Similar to the collection assembly X-Y stage 60 described above, the indexing table X-Y stage 122 includes a Y-axis transport 124 and an X-axis transport 126. The Y-axis transport 124 is automatically, or robotically controllable by the MCS 22 to move the indexing table 24 along the Y-axis of the X-Y-Z coordinate system. Thus, under the control of the MCS 22, the indexing table 24 and associated sorting tray(s) 32 can be automatically positioned anywhere along the length of the Y-axis transport 124. Additionally, the Y-axis transport 124 is movably connected to the X-axis transport 126 of the indexing table X-Y stage 122. Under the control of the MCS 22, the Y-axis transport 124, the indexing table 24 and associated sorting tray(s) 32 can be automatically positioned anywhere along the length of the X-axis transport 126. The staged indexing table 24 can robotically move, as controlled by the MCS 22, along tracks of the X-axis transport 126 and the Y-axis transport 124 utilizing a pneumatically, hydraulically or electrically controlled threaded shaft system, wire or cable pulley system, piston system, or any other suitable positioning system within the X-axis stage 54. Thus, in combination with movement of the nozzle array 36 within the X-Y plane, the sorting tray(s) 32 can be automatically, or robotically, moved in the X and/or Y directions to position any well 34 of the sorting tray(s) 32 under at least one nozzle 40 of the nozzle array 36 to capture and extract the objects from within all the wells 34.

More particularly, the MCS 22 robotically controls movement of the staged indexing table 24 and the nozzle array 36 within the respective X-Y planes to selectively position any and all the sorting tray wells 34 to be offloaded by the offloading subassembly 26. Once the staged indexing table 24 and the nozzle array 36 have been moved within the respective X-Y planes to position the nozzle array 36 above the selected wells 34, the MCS 22 commands the head unit 38 to lower the nozzle array 36 such that the tip 118 of each nozzle 40 is inserted into a corresponding well 34. The MCS 22 then commands one or more selected nozzle regulators 30 to communicate a vacuum pressure, i.e., suction, at the tip 118 of at least one of the nozzles 40. More specifically, one, some or all of the nozzles 40 can be activated by the MCS 22, i.e., provided with a vacuum pressure at the respective tip 118. As described above, the vacuum pressure is utilized by the selected nozzles 40 to capture, i.e., grasp, and retain one or more selected objects in corresponding wells 34. More specifically, one, some or all of the objects in the corresponding wells 34 can be captured and retained by the nozzle array 36. The MCS 22 then commands the head unit 38 to extract the selected objects from the object sorting tray 32. The MCS 22 then moves the staged indexing table 24 to provide an unobstructed path between the nozzle array 36 and the transfer funnel reception end 98.

As described above, the MCS 22 then commands the nozzle array 36 to release selected ones of the extracted objects into the reception end 98 of the transfer funnel 20. Also, as described above, prior to releasing the selected extracted objects, the MCS 22 commands the collection assembly X-Y stage 66 to position a selected one of the receptacles 61 adjacent, e.g., under, the disposition end 102 of the transfer funnel 20 to deposit the selected extracted object(s) in a selected receptacle. The selected extracted object(s) is/are deposited in the selected receptacle(s) 61 based on the specific attributes of the selected extracted object(s).

If not all the extracted objects are to be released and deposited into one selected receptacle, the MCS 22 will command the collection assembly X-Y stage 66 to position a second selected receptacle adjacent the disposition end 102 of the transfer funnel 20 and release at least one of the remaining extracted objects. Thus, the at least one extracted object remaining after the first disposition of selected extracted objects will be deposited into the second selected receptacle, based on the specific attributes of the selected extracted object(s). The MCS 22 will continue to reposition the collection assembly X-Y stage 66, and selectively release and deposit the remaining extracted objects in selected receptacles 61 based on the attributes of each extracted object.

If not all the objects in the sorting tray 32 are extracted during the first extraction process, but it is desired to selectively extract and deposit other objects remaining in the sorting tray 32, the MCS 22 will command repetition of the offloading process, as described above. That is, once the offloading subassembly 26 selectively releases all the objects extracted during a first extraction process, the MCS 22 will reposition the staged indexing table 24 and/or the nozzle array 36 to reposition the sorting tray 32 under the nozzle array 36. The MCS 22 will then command a second selective extraction and disposition of other objects in the sorting tray 32 in the same manner as described above. The MCS 22 will continue to command subsequent selective extraction and disposition processes until all the desired objects in the sorting tray 32 have been selectively extracted and deposited into selected receptacles 61 based on the attributes of the respective selected objects.

Referring to FIGS. 7 and 8, in various embodiments, the extraction assembly 12 includes an indexing table home sensor 128 communicatively connected to the MCS 22. The indexing table home sensor 128 senses when the indexing table 24 is in a home, or start, position. When the indexing table 24 is in the home position, the rotary table is positioned in a desired position for initialization of ASOSS 10 operation. For example, when the rotary indexing table 24 of FIG. 7 is in the home position, the rotary indexing table 24 is positioned such that one end of the rotary indexing table 24 is positioned under the nozzle array 36 and the opposing end is positioned to be accessible for placing, or loading, a sorting tray 32 thereon. Alternatively, when the staged indexing table 24 of FIG. 8 is in the home position, the staged indexing table 24 is positioned such that a center of the staged indexing table 24 is approximately positioned at center of the indexing table X-Y stage 122. Upon initialization of ASOSS 10 operation, the home sensor 128 determines whether the rotary indexing table 24 is in the home position. If the rotary indexing table 24 is sensed to be away from the home position, the MCS 22 will reposition the indexing table 24 to the home position.

Additionally, in various embodiments, the extraction assembly can be utilized to relocate or 're-map' objects within the sorting tray 32. That is, the offloading subassembly 26 can capture and extract one or more objects from the respective sorting tray wells 34, as described above, and relocate, i.e., deposit, the extracted objects to other wells 34 within the sorting tray 32.

Figure 9:
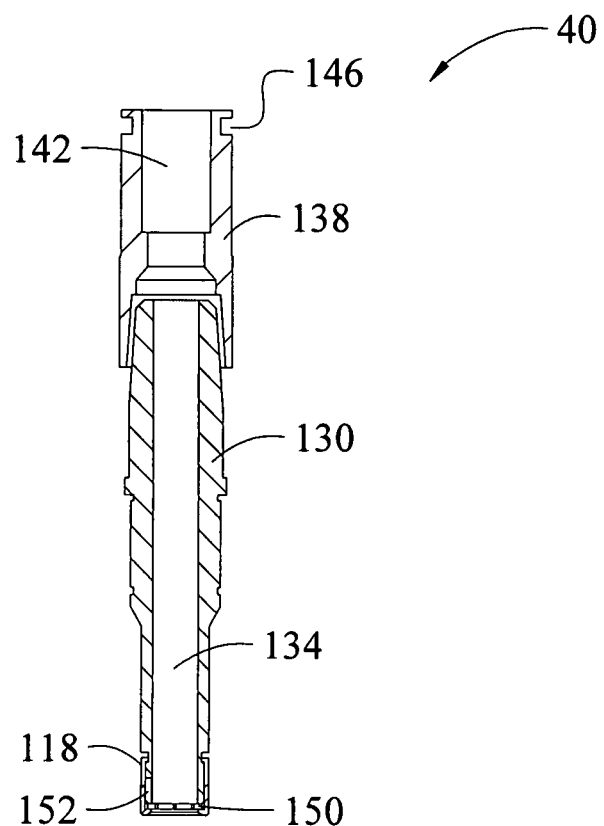
FIG. 9 is a sectional view of one of a plurality of vacuum nozzles included in a nozzle array of the ASOSS shown in FIG. 1, in accordance with various embodiments.

Referring now to FIG. 9, as described above, the nozzle array 36 comprises a plurality of vacuum operated nozzles 40. Generally, each nozzle 40 includes a tubular body 130 having an internal passage 134 defined therewithin. Each nozzle 40 additionally includes a connector cap 138 affixed to, or formed with, a proximal end of the body 130 and having an internal cavity 142 communicatively open to and aligned with the internal passage 134. The connector cap 138 is structured to allow the vacuum flex lines 41 to be removably connected to each respective nozzle connector cap 138. For example, each connector cap 138 can have an annular locking channel 146 around the outside wall of the connector cap 138. Each annular locking channel 146 is structured to receive and lockingly engage an annular slip ring (not shown) of each respective vacuum flex line 134. Therefore, vacuum pressure provided by the respective nozzle regulators 30 is communicated through the respective vacuum flex line 41, the connector cap internal cavity 142 and the nozzle body internal passage 134 to the tip 118 of each respective nozzle 118. More particularly, the vacuum pressure provided at the tip 118 of each nozzle 40 is controlled by at least one respective nozzle regulator 30 that includes switches, valves, and sensors to control and regulate the vacuum pressure at nozzle tip 118 so as to not damage the captured object.

Additionally, in various embodiments, each nozzle tip 118 is customized to optimize handling of each object as it is extracted from the sorting plate and deposited in a receptacle 61 of the receptacle retention apparatus 62. For example, in various embodiments, each tip 118 is structured or formed to accommodate the shape of the wells 34 of the sorting tray 32. For example, if the wells 34 have a shallow, rounded, concave shape, the tip 118 is structured or formed to have wider rounded convex shape such that the tip 118 operates more efficiently when abducting and extracting an object from the wells 34. Or, if the wells 34 have a deeper, cylindrical, flat bottom shape, the tip 118 is structured or formed to have narrow, cylindrical shape with a flat distal end, as shown in FIG. 9, such that the tip 118 operates more efficiently when abducting and extracting an object from the wells 34. Additionally, in various embodiments, the nozzle tips 118 each include a screen-like device 150 having a plurality of openings spaced apart such that the objects can be abducted and extracted without damaging the object. In various embodiments, the tips 118 are interchangeable to meet the handling preferences or requirements of various different objects.

In various embodiments, each nozzle 40 further includes a pressure sensor 152 that senses and monitors the vacuum pressure at the tip 118. More particularly, the pressure sensor 152 communicates vacuum pressure readings at the tip 118 of each nozzle 40 to the MCS 22. The MCS 22 interprets the vacuum pressure readings at each nozzle tip 118 to determine when an object has been successfully captured and extracted from a respective sorting tray well 34 and then also when each extracted object has been released into the transfer funnel 20. For example, prior to capturing and extracting an object, the vacuum pressure at each nozzle tip 118 is sensed to be approximately at a known 'open tip' pressure. When each nozzle 40 of the nozzle array 36 is lowered into the corresponding sorting tray wells 34, if an object resides in the corresponding well, the force of the 'open tip' vacuum pressure will capture the object into the respective nozzle tip 118 and hold the object against the tip 118 and/or the screen-like device 150. Each captured object will obstruct the flow of air through the respective nozzle 40. The obstruction of air flow will alter the vacuum pressure at the respective nozzle tip 118. The respective pressure sensor 152 will sense the change in vacuum pressure and communicate the changed pressure readings to the MCS 22. The MCS 22 will interpret the change in vacuum pressure readings to indicate a 'loaded tip' pressure meaning the respective nozzle 40 has captured the respective object. Then, once the offloading subassembly 26 releases the object into the transfer funnel 20, as described above, the object will no longer obstruct the air flow through the nozzle 40 and the vacuum pressure at the nozzle tip 118 will return to the 'open tip' pressure. The respective pressure sensor 152 will sense the change in vacuum pressure back to the 'open tip' pressure and the MCS 22 will interpret this change back to 'open tip' pressure to indicate that the respective object has been deposited into the selected receptacle 61.

Figure 10:
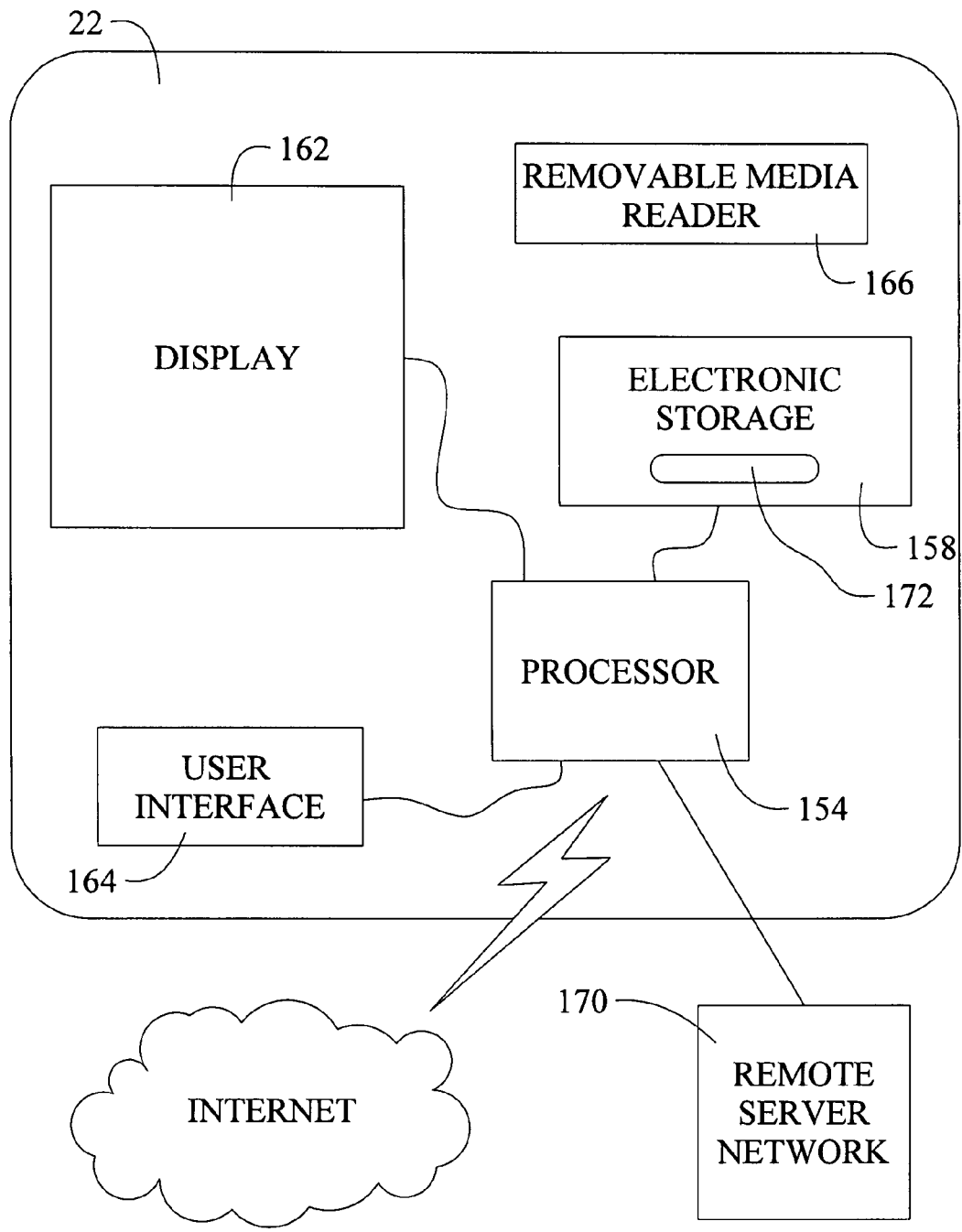
FIG. 10 is a block diagram of a master control system of the ASOSS shown in FIG. 1, in accordance with various embodiments.

Referring to FIG. 10, in various embodiments, the MCS 22 is a computer based system that generally includes at least one processor 154 suitable to execute all functions of MCS 22 to automatically, or robotically, control the operation of the ASOSS 10, as described herein. The MCS 22 additionally includes at least one electronic storage device 158 that comprises a computer readable medium, such as a hard drive or any other electronic data storage device for storing such things as software packages or programs, algorithms and digital information, data, look-up tables, spreadsheets and databases. Furthermore, the MCS 22 includes a display 162 for displaying such things as information, data and/or graphical representations, and at least one user interface device 164, such as a keyboard, mouse, stylus, or an interactive touchscreen on the display 162. In various embodiments the MCS 22 further includes a removable media reader 166 for reading information and data from and/or writing information and data to removable electronic storage media such as floppy disks, compact disks, DVD disks, zip disks, or any other computer readable removable and portable electronic storage media. In various embodiments the removable media reader 166 can be an I/O port of the MCS 22 utilized to read external or peripheral memory devices such as thumb drives or external hard drives.

In various embodiments, the MCS 22, i.e., the processor 154, is communicatively connectable to a remote server network 170, e.g., a local area network (LAN), via a wired or wireless link. Accordingly, the MCS 22 can communicate with the remote server network 170 to upload and/or download data, information, algorithms, software programs, etc., and/or receive ASOSS operational commands from the remote server network 170. Additionally, in various embodiments, the MCS 22 is configured to access the Internet to upload and/or download data, information, algorithms, software programs, etc., to and from Internet sites and network servers.

In various embodiments, the MCS 22 includes an objecting sorting software program 172, stored on the storage device 158 and executed by processor 154 using inputs from the user interface 164 and various components, sensors, systems and assemblies of the ASOSS 10. Execution of object sorting program 172 controls the automated, or robotic, operation of the ASOSS 10.

Figure 11:
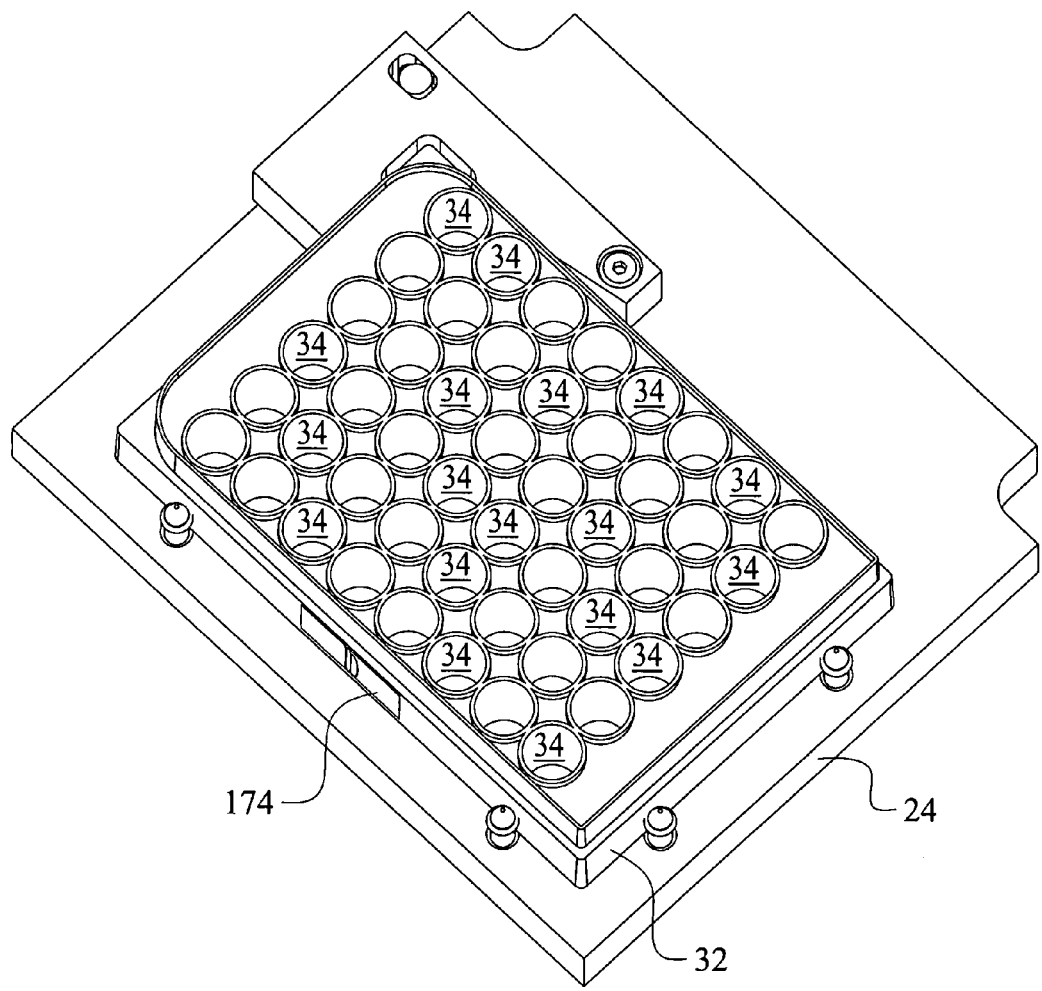
FIG. 11 is an isometric view of a object sorting tray of the ASOSS shown in FIG. 1, in accordance with various embodiments.

Referring now to FIG. 11, as described above, each object sorting tray 32 includes a plurality of wells 34 structured to retain a plurality of objects. Specifically, during operation of the ASOSS 10, some or all of the wells 34 will each have an object retained therein. Additionally, each sorting tray 32 includes a sorting tray identification device 174 attached thereto. The identification device 174 identifies logistic data regarding the respective sorting tray 32. The logistic data is generated based on the specific genotypes or attributes of each particular object in each well 34, e.g., characteristics and/or traits such as size, shape, color, composition, quality, weight, genetic traits, etc. More specifically, in various embodiments, the logistic data includes data and information specifically identifying each object residing in the respective sorting tray 32 based on the specific attributes of each respective object. Additionally, the logistic data includes data identifying the particular well 34 in which each identified object resides. Furthermore, the logistic data includes data identifying the type of receptacle retention apparatus 62 mounted on the collection assembly platform 58 and location, e.g., the X and Y coordinates, of each receptacle 61 within the receptacle retention apparatus 62. Still further yet, the logistic data includes data specifying which specific object(s) residing in the particular sorting tray 32 are to be extracted and deposited into which specific receptacle(s) 61 of the particular receptacle retention apparatus 62. The logistic data can be compiled in any suitable or desirable format, for example, the logistic data can be compiled into one or more electronic databases, spreadsheets and/or look-up tables.

In various embodiments, the logistic data is downloaded to and stored on the electronic storage device 158, such that during execution of the object sorting program 172, by the processor 154, the logistic data is accessed directly, or locally, from the electronic storage device 158 and utilized to control operation of the ASOSS 10, as described herein. In other embodiments, the logistic data can be stored remotely, e.g., on the remote server network 170 or a secure Internet site. Therefore, during execution of the object sorting program 172, the processor 154 is required to access the logistic data from the remote location or site to control operation of the ASOSS 10, as described herein.

In yet other embodiments, the logistic data can be stored on a removable electronic storage media, e.g., floppy disks, compact disks, DVD disks, zip disks, thumb drives, or any other computer readable removable and portable electronic storage media. Therefore, prior to execution of the object sorting program 172 the removable storage media must be inserted or connected to the removable media reader 166. Accordingly, during execution of the object sorting program 172, the processor 154 is required to access the logistic data from the removable media reader 166 to control operation of the ASOSS 10, as described herein. Therefore, during operation of the ASOSS 10, i.e., execution of the object sorting program 172, the processor 154 interprets the logistic data to determine which specific object(s), residing in the particular sorting tray 32 presently supported on the indexing table 24, are to be extracted. Further, the processor 154 interprets the logistic data to determine into which specific receptacle(s) 61, of the particular receptacle retention apparatus 62 mounted on the collection assembly platform 58, the selected objects are to be deposited. Based on these two determinations, the MCS 22, i.e., processor 154, automatically, or robotically, controls the capturing, extraction and disposition of the selected objects in to the specified receptacles 61, as described above.

To initiate execution of the object sorting program 172, and operation of the ASOSS 10, the sorting tray identification, specified by the sorting tray identification device 174, must be input to the MCS 22. Then, based on the sorting tray identification information, the processor 154 accesses the logistic data articulating which specific object(s) are to be deposited into which specific receptacle(s) 61. Then, based on the logistic data, the processor 154 controls operation of the ASOSS 10 to deposit the specified object(s) into the specified receptacle(s) 61, as described above. The sorting tray identification information is input to the MCS 22 using the user interface 164, In various embodiments, the sorting tray identification device 174 is automatically 'read', or interpreted, by the user interface 164 and automatically input to the MCS 22. For example, in various embodiments, the sorting tray identification device 174 comprises a 'bar code' label and the user interface 164 comprises any suitable bar code reader, e.g., a hand held bar code reader. Thus, to initiate operation of the ASOSS 10, a user or operator scans the bar code sorting tray identification device 174 using the bar code reader user interface 164. The processor 154 then interprets the sorting tray identification information provided by reading the bar code sorting tray identification device 174, accesses the logistic data corresponding to the sorting tray identification information, and controls the operation of the ASOSS 10 to extract and deposit the selected object(s) as articulated by the logistic data.

In various other embodiments, the sorting tray identification device 174 can comprise any other sort of 'readable' label and the user interface 164 can comprise any suitable corresponding automated label reader. For example, the sorting tray identification device 174 can comprise a magnetic tag or a magnetic strip readable by a suitable magnetic tag or strip reader user interface 164. Alternatively, the sorting tray identification device 174 can comprise an electronic tag or device readable by a suitable electronic tag or device reader user interface 164. In still other embodiments, the sorting tray identification device 174 can comprise any other sort of human readable or interpretable label. In which case, the user or operator would read human readable sorting tray identification device 174 and manually input the sorting tray identification information directly into the MCS 22 using the user interface 164, e.g., a keyboard, mouse, stylus or touch-screen display.

Referring again to FIGS. 3A, 3B and 3C, in various embodiments, each receptacle 61 includes a receptacle identification tag 178 for identifying the respective receptacle 61 and the selected object to be deposited into the particular receptacle 61. More particularly, in various embodiments, the receptacle identification tags 178 are used to compile the logistic data identifying the location, e.g., X-Y coordinates, of each specific receptacle 61 within the respective receptacle retention apparatus 62. Generally, prior to operation of the ASOSS 10, each receptacle tag 178 is read, or interpreted, and then each receptacle 61 is assigned a position within the receptacle retention apparatus 62. The identification information for each receptacle 61 and the corresponding positions of the receptacles 61 within the receptacle retention apparatus 62 are stored in the MCS 22 as logistic data used during execution of the object sorting program, as described above.

In various embodiments, the receptacle identification tags 178 are automatically 'read', or interpreted, by the user interface 164 and automatically input to the MCS 22. For example, in various embodiments, the receptacle identification tags 178 comprise bar code' labels readable by a bar code reader user interface 164, e.g., a hand held bar code reader. The bar code receptacle identification tags 178 of each receptacle 61 are read utilizing the bar code reader user interface 164.

In various other embodiments, the receptacle identification tags 178 can comprise any other sort of 'readable' label and the user interface 164 can comprise any suitable corresponding automated label reader. For example, the receptacle identification tags 178 can comprise magnetic tags or magnetic strips readable by a suitable magnetic tag or strip reader user interface 164. Alternatively, the receptacle identification tags 178 can comprise electronic tags or devices readable by a suitable electronic tag or device reader user interface 164. In still other embodiments, the receptacle identification tags 178 can comprise any other sort of human readable or interpretable labels or tags. In which case, the user or operator would read human readable receptacle identification tags 178 and manually input the receptacle identification information directly into the MCS 22 using the user interface 164, e.g., a keyboard, mouse, stylus or touch-screen display.

Referring again to FIG. 1, in various embodiments the ASOSS 10 includes at least one emergency stop button 182 accessibly located on ASOSS framework structure 72. Each emergency stop button 182 is communicatively connected to the MCS 22 and/or an electrical power source used to operate the ASOSS 10. During operation of the ASOSS 10, if a situation arises requiring the immediate shut down of the ASOSS 10, an emergency stop button 182 can be depressed to immediately terminate operation of the ASOSS 10. For example, each emergency stop button 182 can transmit a stop command signal to the MCS processor 154 instructing the processor 154 to terminate operation of the ASOS 10. Alternatively, or additionally, each emergency stop button 182 can include a switch that breaks or disconnects the flow of electricity to ASOSS 10, thereby terminating electrical power necessary for the ASOSS 10 to operate.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. An automated small object sorting system comprising:
   an object sorting tray configured to hold a plurality of objects;
   a transfer funnel;
   an automated object extraction assembly, comprising:
   an automated object offloading mechanism including a nozzle array having a plurality of nozzles, the nozzles of the automated object offloading mechanism connectable to a vacuum source to selectively provide a vacuum pressure at a tip of each nozzle; and
   an automated moveable indexing table configured to support the object sorting tray, the indexing table operable to position the object sorting tray over the transfer funnel, and the nozzles of the automated object offloading mechanism configured to extract, via the vacuum pressure, one or more objects from the object sorting tray and deposit the one or more extracted objects into a reception end of the transfer funnel;
   multiple collection receptacles configured to receive the one or more extracted objects from the transfer funnel;
   an automated collection assembly configured to selectively position one or more of the collection receptacles under the object sorting tray: the collection assembly comprising a receptacle retention apparatus structured to removably retain the collection receptacles, and mounted on an automated X-Y stage configured to position the receptacle retention apparatus such that the selected collection receptacle is positioned adjacent a disposition end of the transfer funnel, in accordance with the one or more extracted objects to be deposited into the transfer funnel; and
   at least one processor based master control system operable to control the object offloading mechanism and nozzle array utilizing electronically stored logistic data to stipulate specific ones of the nozzles to which vacuum pressure is to be provided such that selected ones of objects in the object sorting tray are extracted,
   wherein the logistic data comprises data identifying particular traits or characteristics of each object in the sorting tray and the location of each respective object within the sorting tray such that the at least one master control system commands the offloading mechanism and nozzle array to extract the selected objects based on the traits or characteristics of each respective object;
   wherein the transfer funnel is disposed below the indexing table and at least partly within a footprint defined by the indexing table when the object sotring tray is in the position for the array of extraction nozzles to remove, at about the same time, the one or more objects from the object sorting tray.

2. The system of claim 1 wherein the indexing table comprises at least one automated actuator configured to hold the object sorting tray in position on the indexing table.

3. The system of claim 1 wherein the at least one processor based master control system is adapted to control operation of the system utilizing the electronically stored logistic data to stipulate the specific collection receptacle into which to deposit each extracted object.

4. The system of claim 1 wherein the object sorting tray comprises an identification device coupled thereto that provides the logistic data for each object within the object sorting tray.

5. The system of claim 1 wherein the nozzle array is interchangeably connected to an automated head unit of the offloading mechanism, the head unit structured to move the nozzle array within an X-Y-Z coordinate system to extract the one or more objects from the object sorting tray.

6. The system of claim 1 wherein each nozzle includes a custom tip structured to handle each object as it is extracted from the object sorting tray and deposited into the transfer funnel without causing damage to each respective object.

7. The system of claim 1, wherein the nozzles are geometrically arranged in the array such that a spacing between adjacent nozzles corresponds with a spacing between adjacent wells of the object sorting tray tray.

8. The system of claim 1, wherein the indexing table is configured to rotate the object sorting tray into position for the array of nozzles to remove, at about the same time, multiple objects from the object sorting tray.

9. The system of claim 1, wherein the indexing table is configured to move the object sorting tray in at least two different directions.

10. The system of claim 1, wherein the X-Y stage is disposed below the indexing table.

11. The system of claim 1, wherein the transfer funnel includes at least two internal passages for directing objects through the funnel.

12. The system of claim 1, wherein the indexing table is configured to selectively rotate the object sorting tray into a position over the transfer funnel for the nozzles of the offloading assembly to remove objects from the object sorting tray.

13. The system of claim 1, wherein the nozzles are geometrically arranged in the array and operable to move together as a group to remove, at about the same time, multiple objects from the object sorting tray.

14. The system of claim 1 wherein the indexing table is operable to:

move the object sorting tray to a first position in which the object sorting tray is above the transfer funnel so that the automated object extraction assembly can extract the one or more objects from the object sorting tray;

move the object sorting tray to a second position so that the automated object extraction assembly can deposit the at least one or more extracted objects into the reception end of the transfer funnel; and move the object sorting tray back to the first position so that the automated object extraction assembly can extract one or more additional objects from the object sorting tray.

15. The system of claim 1 wherein the indexing table is operable to:

move the object sorting tray into the position over the transfer funnel so that the automated object extraction assembly can extract the one or more objects from the object sorting tray;

move the object sorting tray into a position away from the transfer funnel so that the automated object extraction assembly can deposit the at least one or more extracted objects into the transfer funnel; and move the object sorting tray back into the position over the transfer funnel so that the automated object extraction assembly can extract one or more additional objects from the object sorting tray.

16. The system of claim 1 wherein the nozzles of the object offloading assembly are operable to remove, at about the same time, multiple objects from the object sorting tray.

17. The system of claim 1, wherein the X-Y stage is located below at least part of the indexing table and at least partly within a footprint defined by the indexing table, and wherein the transfer funnel is located between the indexing table and the X-Y stage and at least partly within the footprint defined by the indexing table.

* * * * *